(12) United States Patent
De Lombaert et al.

(10) Patent No.: US 8,772,304 B2
(45) Date of Patent: Jul. 8, 2014

(54) BENZIMIDAZOLE INHIBITORS OF LEUKOTRIENE PRODUCTION

(75) Inventors: Stephane De Lombaert, Branford, CT (US); Weimin Liu, Beijing (CN); Ho Yin Lo, Bethel, CT (US); Peter Allen Nemoto, Southbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 164 days.

(21) Appl. No.: 13/281,687

(22) Filed: Oct. 26, 2011

(65) Prior Publication Data

US 2012/0277227 A1 Nov. 1, 2012

Related U.S. Application Data

(60) Provisional application No. 61/408,740, filed on Nov. 1, 2010.

(51) Int. Cl.
*C07D 401/14* (2006.01)
*A61K 31/4184* (2006.01)

(52) U.S. Cl.
USPC ............ 514/275; 514/333; 544/331; 546/256

(58) Field of Classification Search
USPC .................... 544/331; 546/256; 514/275, 333
See application file for complete search history.

(56) References Cited

U.S. PATENT DOCUMENTS

| | | | |
|---|---|---|---|
| 4,923,869 A * | 5/1990 | Prucher et al. ........... | 514/252.03 |
| 6,911,444 B2 | 6/2005 | Lacrampe et al. | |
| 7,138,420 B2 | 11/2006 | Bentzien et al. | |
| 7,151,114 B2 | 12/2006 | Streicher et al. | |
| 7,319,108 B2 | 1/2008 | Schwink et al. | |
| 8,420,655 B2 | 4/2013 | Chen et al. | |
| 2005/0187390 A1 * | 8/2005 | Schmitz et al. ............... | 544/310 |
| 2011/0301161 A1 | 12/2011 | Chen et al. | |

FOREIGN PATENT DOCUMENTS

| | | |
|---|---|---|
| EP | 0193013 A2 | 9/1986 |
| WO | 9961020 A1 | 12/1999 |
| WO | 2005012288 A1 | 2/2005 |
| WO | 2006044602 A2 | 4/2006 |
| WO | 2007056228 A2 | 5/2007 |
| WO | 2007120574 A2 | 10/2007 |
| WO | 2008030369 A1 | 3/2008 |
| WO | 2008067644 A1 | 6/2008 |
| WO | 2008128335 A1 | 10/2008 |
| WO | 2008156721 A1 | 12/2008 |
| WO | 2009048547 A1 | 4/2009 |
| WO | 2011068821 A1 | 6/2011 |
| WO | 2011143466 A1 | 11/2011 |

OTHER PUBLICATIONS

Gura et al., Systems for identifying new drugs are often faulty, Science, 278:1041-1042, 1997.*

Johnson et al., Relationships between drug activity in NCI preclinical in vitro and in vivo models and early clinical trials, British Journal of Cancer, 84(10):1424-1431, 2001.*

Simone, Oncology: Introduction, Cecil Textbook of Medicine, 20th Edition, vol. 1, pp. 1004-1010, 1996.*

Pearce et al., Failure modes in anticancer drug discovery and development, Cancer Drug Design and Discovery Edited by Stephen Neidle, Chapter 18, pp. 424-435 (2008).*

International Search Report for PCT/US2010/058479 mailed Feb. 25, 2011.

International Search Report for PCT/US2011/057786 mailed on Dec. 19, 2011.

International Search Report for PCT/US2011/057787 mailed Mar. 21, 2012.

U.S. Appl. No. 13/281,685, filed Oct. 26, 2011. Inventor: Zhidong Chen.

Werz, Oliver et al. "Pharmacological intervention with 5-lipoxygenase: new insights and novel compounds" Expert Opin. Ther. Patents (2005) 15(5) pp. 505-519.

* cited by examiner

*Primary Examiner* — Deepak Rao
(74) *Attorney, Agent, or Firm* — Michael P. Morris; Usha R. Patel

(57) ABSTRACT

The present invention relates to compounds of formula (IA), (IB) and (IC):

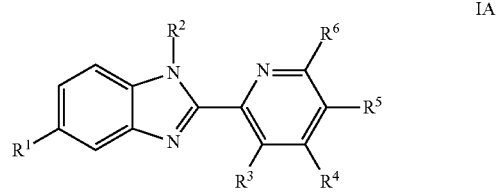

IA

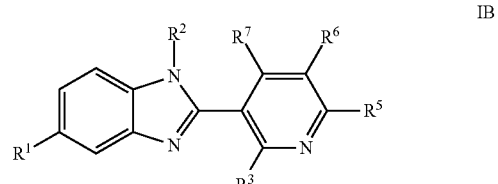

IB

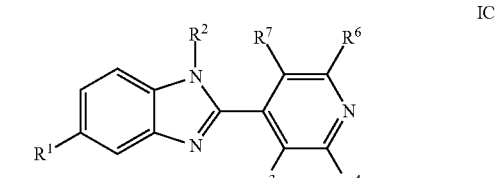

IC and pharmaceutically acceptable salts thereof, wherein $R^1$-$R^7$ are as defined herein. The invention also relates to pharmaceutical compositions comprising these compounds, methods of using these compounds in the treatment of various diseases and disorders, processes for preparing these compounds and intermediates useful in these processes.

34 Claims, No Drawings

BENZIMIDAZOLE INHIBITORS OF LEUKOTRIENE PRODUCTION

FIELD OF THE INVENTION

This invention relates to benzimidazoles that are useful as inhibitors of five lipoxygenase activating protein (FLAP) and are thus useful for treating a variety of diseases and disorders that are mediated or sustained through the activity of leukotrienes including asthma, allergy, rheumatoid arthritis, multiple sclerosis, inflammatory pain, acute chest syndrome and cardiovascular diseases including atherosclerosis, myocardial infarction and stroke. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Leukotrienes (LTs) and the biosynthetic pathway from arachidonic acid leading to their production have been the targets of drug discovery efforts for over twenty years. LTs are produced by several cell types including neutrophils, mast cells, eosinophils, basophils monocytes and macrophages. The first committed step in the intracellular synthesis of LTs involves oxidation of arachidonic acid by 5-lipoxygenase (5-LO) to LTA4, a process requiring the presence of the 18 kD integral membrane protein 5-lipoxygenase-activating protein (FLAP) (D. K. Miller et al., Nature, 1990, 343, 278-281; R. A. F. Dixon et al., Nature, 1990, 343, 282-284). Subsequent metabolism of $LTA_4$ leads to $LTB_4$, and the cysteinyl LTs-$LTC_4$, $LTD_4$ and $LTE_4$ (B. Samuelsson, Science, 1983, 220, 568-575). The cysteinyl LTs have potent smooth muscle constricting and bronchoconstricting effects and they stimulate mucous secretion and vascular leakage. $LTB_4$ is a potent chemotactic agent for leukocytes, and stimulates adhesion, aggregation and enzyme release.

Much of the early drug discovery effort in the LT area was directed towards the treatment of allergy, asthma and other inflammatory conditions. Research efforts have been directed towards numerous targets in the pathway including antagonists of $LTB_4$ and the cysteinyl leukotrienes $LTC_4$, $LTD_4$ and $LTE_4$, as well as inhibitors of 5-lipoxygenase (5-LO), $LTA_4$ hydrolase and inhibitors of 5-lipoxygenase activating protein (FLAP) (R. W. Friesen and D. Riendeau, Leukotriene Biosynthesis Inhibitors, Ann. Rep. Med. Chem., 2005, 40, 199-214). Years of effort in the above areas have yielded a few marketed products for the treatment of asthma including a 5-LO inhibitor, zileuton, and LT antagonists, montelukast, pranlukast and zafirlukast.

More recent work has implicated LTs in cardiovascular disease, including myocardial infarction, stroke and atherosclerosis (G. Riccioni et al., J. Leukoc. Biol., 2008, 1374-1378). FLAP and 5-LO were among the components of the 5-LO and LT cascade found in atherosclerotic lesions, suggesting their involvement in atherogenesis (R. Spanbroek et al., Proc. Natl. Acad. Sci. U.S.A., 2003, 100, 1238-1243). Pharmacological inhibition of FLAP has been reported to decrease atherosclerotic lesion size in animal models. In one study, oral dosing of the FLAP inhibitor MK-886 to apoE/LDL-R double knockout mice fed a high-fat diet from 2 months of age to 6 months led to a 56% decrease in plaque coverage in the aorta and a 43% decrease in the aortic root (J. Jawien et al., Eur. J. Clin. Invest., 2006, 36, 141-146). This plaque effect was coupled with a decrease in plaque-macrophage content and a concomitant increase in collagen and smooth muscle content which suggests a conversion to a more stable plaque phenotype. In another study, it was reported that administration of MK-886 via infusion to ApoE$^{-/-}$ xCD4dnTβRII mice (apoE KO mice expressing a dominant-negative TGF-beta receptor which effectively removes all TGF-beta from the system) resulted in about a 40% decrease in plaque area in the aortic root (M. Back et al., Circ. Res., 2007, 100, 946-949). The mice were only treated for four weeks after plaque growth was already somewhat mature (12 weeks) thus raising the possibility of therapeutically treating atherosclerosis via this mechanism. In a study examining human atherosclerotic lesions, it was found that the expression of FLAP, 5-LO and $LTA_4$ hydrolase was significantly increased compared to healthy controls (H. Qiu et al., Proc. Natl. Acad. Sci. U.S.A., 103, 21, 8161-8166). Similar studies suggest that inhibition of the LT pathway, for example by inhibition of FLAP, would be useful for the treatment of atherosclerosis (for reviews, see M. Back Curr. Athero. Reports, 2008 10, 244-251 and Curr. Pharm. Des., 2009, 15, 3116-3132).

In addition to the work cited above, many other studies have been directed towards understanding the biological actions of LTs and the role of LTs in disease. These studies have implicated LTs as having a possible role in numerous diseases or conditions (for a review, see M. Peters-Golden and W. R. Henderson, Jr., M. D., N. Engl. J. Med., 2007, 357, 1841-1854). In addition to the specific diseases cited above, LTs have been implicated as having a possible role in numerous allergic, pulmonary, fibrotic, inflammatory and cardiovascular diseases, as well as cancer. Inhibition of FLAP is also reported to be useful for treating renal diseases such as diabetes-induced proteinuria (see for example J. M. Valdivieso et al., Journal of Nephrology, 2003, 16, 85-94 and A Montero et al., Journal of Nephrology, 2003, 16, 682-690).

A number of FLAP inhibitors have been reported in the scientific literature (see for example J. F. Evans et al., Trends in Pharmacological Sciences, 2008, 72-78) and in U.S. patents. Some have been evaluated in clinical trials for asthma, including MK-886, MK-591, and BAY X1005, also known as DG-031. More recently, the FLAP inhibitor AM-103 (J. H. Hutchinson et al., J. Med. Chem. 52, 5803-5815) has been evaluated in clinical trials, based on its anti-inflammatory properties (D. S. Lorrain et al., J. Pharm. Exp. Ther., 2009, DOI:10.1124/jpet.109.158089). Subsequently, it was replaced by the back-up compound AM-803 (GSK-2190915) for the treatment of respiratory diseases. DG-031 has also been in clinical trials to evaluate its effect on biomarkers for myocardial infarction risk and showed a dose-dependent suppression of several biomarkers for the disease (H. Hakonarson et al., JAMA, 2005, 293, 2245-2256). MK-591 was shown in a clinical trial to reduce proteinuria in human glomerulonephritis (see for example A. Guash et al., Kidney International, 1999, 56, 291-267).

However, to date, no FLAP inhibitor has been approved as a marketed drug.

BRIEF SUMMARY OF THE INVENTION

The present invention provides novel compounds which inhibit 5-lipoxygenase activating protein (FLAP) and are thus useful for treating a variety of diseases and disorders that are mediated or sustained through the activity of leukotrienes, including allergic, pulmonary, fibrotic, inflammatory and cardiovascular diseases and cancer. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In its first broadest embodiment, the present invention relates to a compound of formula IA

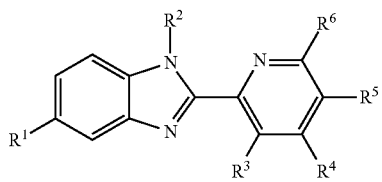

wherein:
$R^1$ is pyridinyl, pyrimidinyl, pyrazinyl, pyridazinyl, pyrrolopyridinyl, imidazopyridinyl, pyrazolopyridinyl or dihydropyrrolopyridinyl optionally substituted with oxo, wherein each heterocycle is optionally independently substituted with one to three groups selected from Ra, Rb and Rc;
$R^2$ is $C_1$-$C_6$ alkyl or $C_{3-6}$ cycloalkyl optionally substituted with $C_{1-3}$ alkyl;
$R^3$ is H, —OH, halogen, —CN, $C_{1-6}$ alkoxy, —COOR$^8$, —C(O)NR$^8$R$^9$ or 5-6 membered heteroaryl ring which is optionally substituted with $C_{1-3}$ alkyl;
$R^4$, $R^5$, and $R^6$ are each independently selected from
(a) —H,
(b) —OH,
(c) halogen,
(d) —CN,
(e) —CF$_3$,
(f) $C_{1-6}$alkyl optionally substituted with one to three —OH, fluorine, $C_{1-6}$alkoxyl —N(R$^8$)(R$^9$), or —C(O)N(R$^8$)(R$^9$),
(g) $C_{3-6}$ cycloalkyl
(h) $C_{1-6}$alkoxy optionally substituted with one to three —OH, fluorine, —OC$_{1-6}$alkyl, or —OC$_{3-6}$ cycloalkyl
(i) —S(O)$_n$C$_{1-6}$alkyl,
(j) —S(O)$_2$aryl
(k) —S(O)$_2$heterocycle
(l) —CO$_2$R$^8$,
(m) —SCF$_3$,
(n') a 5-6 membered heterocyclic ring;
$R^8$ and $R^9$ are each independently selected from —H, $C_{1-6}$alkyl, and 5-6 membered heterocyclic ring;
Ra is selected from H, —NH$_2$, —NH(C$_1$-C$_6$)alkyl, —NR$^{10}$R$^{11}$, —NH—C(O)C$_1$-C$_6$alkyl, NR$^{11}$—C(O)C$_1$-C$_6$alkyl, —O(C$_1$-C$_8$)alkyl, —O(C$_3$-C$_6$)cycloalkyl, —S—(C$_1$-C$_6$)alkyl, —S(O)—C$_1$-C$_6$alkyl, —S(O)$_2$—C$_1$-C$_6$alkyl, and —CH$_2$—OH;
Rb is selected from —H, —(C$_1$-C$_6$)alkyl, —O—(C$_1$-C$_6$) alkyl, —NH$_2$, —CH$_2$—OH, —C≡N, —CH$_2$NH$_2$ and —C(O)OCH$_3$;
Rc is selected from —H, —CH$_3$ and —OH;
$R^{10}$ and $R^{11}$ are each independently selected from —H, $C_{1-6}$alkyl, $C_{1-6}$alkyl-5-6 membered heterocyclyl, $C_{1-6}$alkyl-5-6 membered heteroaryl optionally substituted with halogen and $C_{1-6}$alkyl-aryl;
n is 0, 1 or 2;
or a pharmaceutically acceptable salt thereof.

In a second embodiment, the present invention relates to a compound of formula (IA) as described in the broadest embodiment above, or a pharmaceutically acceptable salt thereof, wherein:
$R^1$ is selected from:

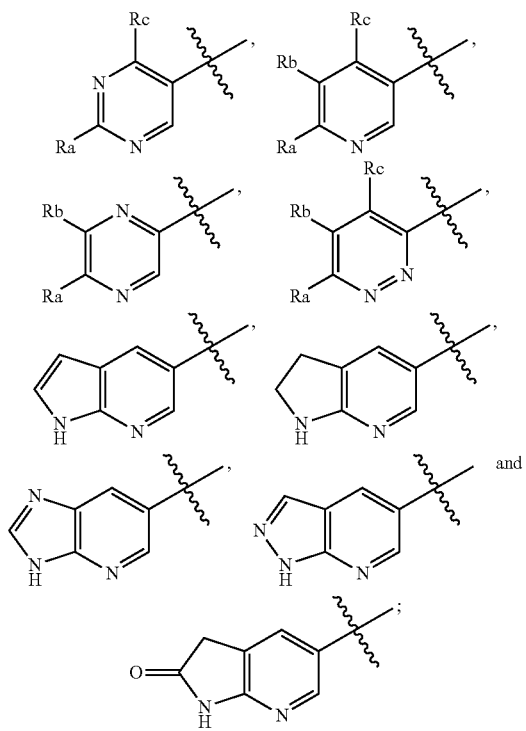

$R^2$ is methyl, ethyl, propyl, isopropyl, butyl, t-butyl, isobutyl, pentyl, hexyl, cyclopropyl, cyclobutyl, cyclopentyl or cyclohexyl, wherein the cycloalkyl group is optionally substituted with a $C_{1-3}$ alkyl group;
$R^3$ is H, —OH, halogen, —CN, $C_{1-6}$ alkoxy, —COOR$^8$, —C(O)NR$^8$R$^9$, pyrrolyl, furanyl, thienyl, imidazolyl, pyrazolyl, triazolyl, pyridinyl, pyrimidinyl, pyrazinyl or pyridazinyl, wherein the heteroaryl ring is optionally substituted with $C_{1-3}$ alkyl;
$R^4$, $R^5$ and $R^6$ are each independently selected from
(a) —H,
(b) —OH,
(c) halogen,
(d) —CN,
(e) —CF$_3$,
(f) $C_{1-6}$alkyl optionally substituted with one to three —OH, fluorine, $C_{1-6}$alkoxyl —N(R$^8$)(R$^9$), or —C(O)N(R$^8$)(R$^9$),
(g) $C_{3-6}$ cycloalkyl
(h) $C_{1-6}$alkoxy optionally substituted with one to three —OH, fluorine, —OC$_{1-6}$alkyl, or —OC$_{3-6}$ cycloalkyl
(i) —S(O)$_n$C$_{1-6}$alkyl,
(j) —S(O)$_2$aryl
(k) —S(O)$_2$heterocycle
(l) —CO$_2$R$^8$,
(m) —SCF$_3$,
(n') a pyrrolidinyl, tetrahydrofuranyl, tetrahydrothienyl, piperidinyl, morpholinyl, thiomorpholinyl, dioxothiomorpholinyl and tetrahydropyranyl;
$R^8$ and $R^9$ are each independently selected from —H, $C_{1-6}$alkyl, pyrrolidinyl, tetrahydrofuranyl, tetrahydrothienyl, piperidinyl, morpholinyl, thiomorpholinyl, dioxothiomorpholinyl and tetrahydropyranyl;

Ra is selected from H, —NH$_2$, —NH(C$_1$-C$_6$)alkyl, —NR$^{10}$R$^{11}$, —NH—C(O)C$_1$-C$_6$alkyl, NR$^{11}$—C(O)C$_1$-C$_6$alkyl, —O(C$_1$-C$_8$)alkyl, —O(C$_3$-C$_6$)cycloalkyl, —S—(C$_1$-C$_6$)alkyl, —S(O)—C$_1$-C$_6$alkyl, —S(O)$_2$—C$_1$-C$_6$alkyl and —CH$_2$—OH;

Rb is selected from —H, —(C$_1$-C$_6$)alkyl, —O—(C$_1$-C$_6$)alkyl, —NH$_2$, —CH$_2$—OH, —C≡N, —CH$_2$NH$_2$ and —C(O)OCH$_3$;

Rc is selected from —H, —CH$_3$ and, —OH;

R$^{10}$ and R$^{11}$ are each independently selected from —H, C$_{1-6}$alkyl, C$_{1-6}$alkyl-5-6 membered heterocyclyl, C$_{1-6}$alkyl-5-6 membered heteroaryl optionally substituted with fluoro and C$_{1-6}$alkyl-phenyl;

n is 0, 1 or 2.

In third embodiment, the present invention relates to a compound of formula (IA) as described in any of the preceding embodiments, wherein:
R$^1$ is selected from:

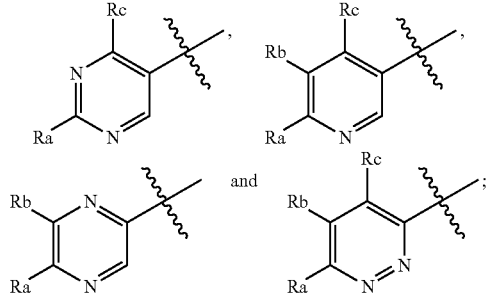

Ra is selected from H, —NH$_2$, —NH(C$_1$-C$_6$)alkyl, —NR$^{10}$R$^{11}$, —NH—C(O)C$_1$-C$_6$alkyl, NR$^{11}$—C(O)C$_1$-C$_6$alkyl, —O(C$_1$-C$_8$)alkyl, —O(C$_3$-C$_6$)cycloalkyl, —S—(C$_1$-C$_6$)alkyl, —S(O)—C$_1$-C$_6$alkyl, —S(O)$_2$—C$_1$-C$_6$alkyl and —CH$_2$—OH;

Rb is selected from —H, —(C$_1$-C$_6$)alkyl, —O—(C$_1$-C$_6$)alkyl, —NH$_2$, —CH$_2$—OH, —C≡N, —CH$_2$NH$_2$ and —C(O)OCH$_3$;

Rc is selected from —H, —CH$_3$ and, —OH;

R$^{10}$ and R$^{11}$ are each independently selected from —H, C$_{1-6}$alkyl, C$_{1-6}$alkyl-5-6 membered heterocyclyl, C$_{1-6}$alkyl-fluorpyridine and C$_{1-6}$alkyl-phenyl;

or a pharmaceutically acceptable salt thereof.

In a fourth embodiment there is provided a compound of formula (IA) as described in any of the preceding embodiments above, wherein:
R$^2$ is methyl, ethyl, propyl, isopropyl, butyl, t-butyl, isobutyl, cyclopropyl, cyclobutyl or cyclopentyl, wherein the cycloalkyl group is optionally substituted with methyl;

or a pharmaceutically acceptable salt thereof.

In a fifth embodiment there is provided a compound of formula (IA) as described in any of the preceding embodiments, wherein:
R$^3$ is H, —OH, halogen, —CN, C$_{1-6}$ alkoxy, —COOR$^8$, —C(O)NR$^8$R$^9$, pyrrolyl, furanyl, thienyl, imidazolyl, pyrazolyl, triazolyl, pyridinyl, pyrimidinyl, pyrazinyl or pyridazinyl, wherein the heteroaryl ring is optionally substituted with C$_{1-3}$ alkyl;

R$^4$, R$^5$ and R$^6$ are each independently selected from
(a) —H,
(b) —OH,
(c) halogen,
(d) —CN,
(e) —CF$_3$,
(f) C$_{1-6}$alkyl optionally substituted with one to three —OH, fluorine, C$_{1-6}$alkoxyl —N(R$^8$)(R$^9$), or —C(O)N(R$^8$)(R$^9$),
(g) C$_{3-6}$ cycloalkyl
(h) C$_{1-6}$alkoxy optionally substituted with one to three —OH, fluorine, —OC$_{1-6}$alkyl, or —OC$_{3-6}$ cycloalkyl
(i) —S(O)$_2$C$_{1-6}$alkyl,
(j) —S(O)$_2$aryl
(k) —S(O)$_2$ heterocycle
(l) —CO$_2$R$^8$,
(m) —SCF$_3$,
(n') a pyrrolidinyl, tetrahydrofuranyl, tetrahydrothienyl, piperidinyl, morpholinyl, thiomorpholinyl, dioxothiomorpholinyl and tetrahydropyranyl;

R$^8$ and R$^9$ are each independently selected from —H, C$_{1-6}$alkyl, pyrrolidinyl, tetrahydrofuranyl, tetrahydrothienyl, piperidinyl, morpholinyl, thiomorpholinyl, dioxothiomorpholinyl and tetrahydropyranyl;

or a pharmaceutically acceptable salt thereof.

In a sixth embodiment there is provided a compound of formula (IA) as described in the first or second embodiment above, wherein:
R$^1$ is selected from:

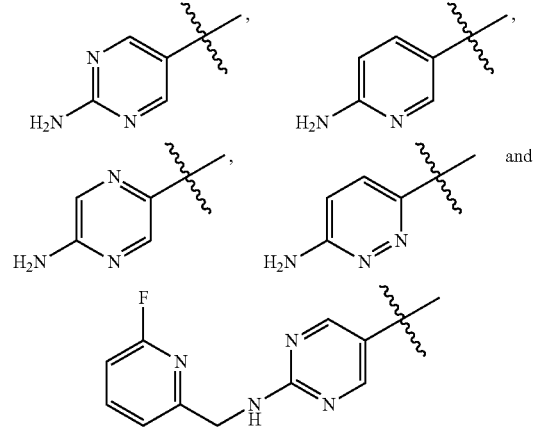

R$^2$ is t-butyl or cyclobutyl optionally substituted with a methyl group;
R$^3$ is —H, C$_{1-3}$ alkoxy, —COOR$^8$, —C(O)NR$^8$R$^9$ or triazolyl which is optionally substituted with a methyl group;
R$^4$, R$^5$ and R$^6$ are each independently selected from
(a) —H,
(b) —OH,
(c) halogen,
(d) —CN,
(e) —CF$_3$,
(f) C$_{1-6}$alkyl optionally substituted with one to three —OH, fluorine, C$_{1-6}$alkoxyl —N(R$^8$)(R$^9$), or —C(O)N(R$^8$)(R$^9$),
(g) C$_{3-6}$ cycloalkyl
(h) C$_{1-6}$alkoxy optionally substituted with one to three —OH, fluorine, —OC$_{1-6}$alkyl, or —OC$_{3-6}$ cycloalkyl;
R$^8$ and R$^9$ are each independently selected from —H and C$_{1-6}$alkyl;

or a pharmaceutically acceptable salt thereof.

In a seventh embodiment there is provided a compound of formula (IA) as described in the sixth embodiment above, or a pharmaceutically acceptable salt thereof, wherein R¹ is

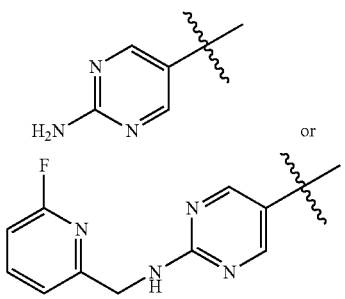

In an eighth embodiment there is provided a compound of formula (IA) as described in the sixth embodiment above, wherein:
R² is t-butyl or cyclobutyl optionally substituted with a methyl group;
or a pharmaceutically acceptable salt thereof.

In a ninth embodiment there is provided a compound of formula (IA) according to embodiment six, wherein:
R¹ is

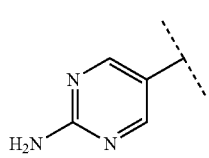

R² is t-butyl;
R³ is selected from

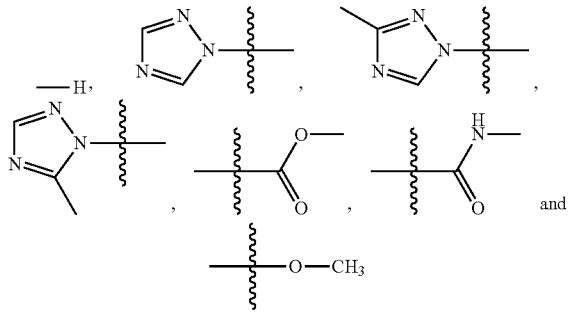

R⁴, R⁵ and R⁶ are each independently selected from —H, —CN, F, cyclopropyl, methoxy and t-butoxy;
or a pharmaceutically acceptable salt thereof.

In a tenth embodiment there is provided a compound of formula (IA) according to embodiment nine above, wherein:
R² is

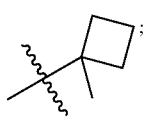

or a pharmaceutically acceptable salt thereof.

In another first broadest embodiment, the present invention relates to a compound of formula IB

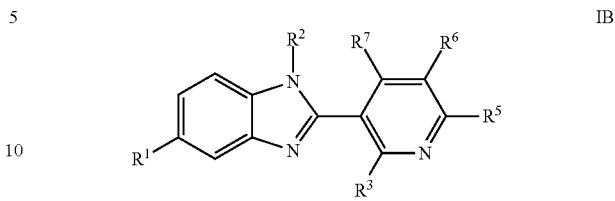

wherein:
R¹ is pyridinyl, pyrimidinyl, pyrazinyl, pyridazinyl, pyrrolopyridinyl, imidazopyridinyl, pyrazolopyridinyl or dihydropyrrolopyridinyl optionally substituted with oxo, wherein each heterocycle is optionally independently substituted with one to three groups selected from Ra, Rb and Rc;
R² is $C_1$-$C_6$ alkyl or $C_{3-6}$ cycloalkyl optionally substituted with $C_{1-3}$ alkyl;
R³ is H, —OH, halogen, —CN, $C_{1-6}$ alkoxy, —COOR⁸, —C(O)NR⁸R⁹ or 5-6 membered heteroaryl ring which is optionally substituted with $C_{1-3}$ alkyl;
R⁵, R⁶, and R⁷ are each independently selected from
(a) —H,
(b) —OH,
(c) halogen,
(d) —CN,
(e) —CF₃,
(f) $C_{1-6}$alkyl optionally substituted with one to three —OH, fluorine, $C_{1-6}$alkoxyl —N(R⁸)(R⁹), or —C(O)N(R⁸)(R⁹),
(g) $C_{3-6}$ cycloalkyl
(h) $C_{1-6}$alkoxy optionally substituted with one to three —OH, fluorine, —O$C_{1-6}$alkyl, or —O$C_{3-6}$ cycloalkyl
(i) —S(O)ₙ$C_{1-6}$alkyl,
(j) —S(O)₂aryl
(k) —S(O)₂ heterocycle
(l) —CO₂R⁸,
(m) —SCF₃,
(n') a 5-6 membered heterocyclic ring;
R⁸ and R⁹ are each independently selected from —H, $C_{1-6}$alkyl, and 5-6 membered heterocyclic ring;
Ra is selected from H, —NH₂, —NH($C_1$-$C_6$)alkyl, —NR¹⁰R¹¹, —NH—C(O)$C_1$-$C_6$alkyl, NR¹¹—C(O)$C_1$-$C_6$alkyl, —O($C_1$-$C_8$)alkyl, —O($C_3$-$C_6$)cycloalkyl, —S—($C_1$-$C_6$)alkyl, —S(O)—$C_1$-$C_6$alkyl, —S(O)₂—$C_1$-$C_6$alkyl, and —CH₂—OH;
Rb is selected from —H, —($C_1$-$C_6$)alkyl, —O—($C_1$-$C_6$)alkyl, —NH₂, —CH₂—OH, —C≡N, —CH₂NH₂ and —C(O)OCH₃;
Rc is selected from —H, —CH₃ and, —OH;
R¹⁰ and R¹¹ are each independently selected from —H, $C_{1-6}$alkyl, $C_{1-6}$alkyl-5-6 membered heterocyclyl, $C_{1-6}$alkyl-5-6 membered heteroaryl optionally substituted with halogen and $C_{1-6}$alkyl-aryl;
n is 0, 1 or 2;
or a pharmaceutically acceptable salt thereof.

In a second embodiment, the present invention relates to a compound of formula (TB) as described in the broadest embodiment above, or a pharmaceutically acceptable salt thereof, wherein:
$R^1$ is selected from:

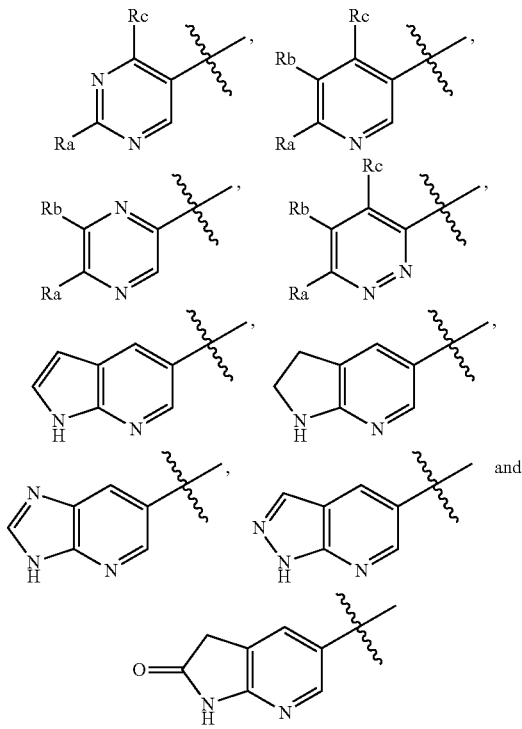

$R^2$ is methyl, ethyl, propyl, isopropyl, dimethylpropyl, butyl, t-butyl, isobutyl, pentyl, hexyl, cyclopropyl, cyclobutyl, cyclopentyl or cyclohexyl, wherein the cycloalkyl group is optionally substituted with a $C_{1-3}$ alkyl group;

$R^3$ is H, —OH, halogen, —CN, $C_{1-6}$ alkoxy, —COOR$^8$, —C(O)NR$^8$R$^9$, pyrrolyl, furanyl, thienyl, imidazolyl, pyrazolyl, triazolyl, pyridinyl, pyrimidinyl, pyrazinyl or pyridazinyl, wherein the heteroaryl ring is optionally substituted with $C_{1-3}$ alkyl;

$R^5$, $R^6$ and $R^7$ are each independently selected from
(a) —H,
(b) —OH,
(c) halogen,
(d) —CN,
(e) —CF$_3$,
(f) $C_{1-6}$ alkyl optionally substituted with one to three —OH, fluorine, $C_{1-6}$ alkoxyl —N(R$^8$)(R$^9$), or —C(O)N(R$^8$)(R$^9$),
(g) $C_{3-6}$ cycloalkyl
(h) $C_{1-6}$ alkoxy optionally substituted with one to three —OH, fluorine, —OC$_{1-6}$alkyl, or —OC$_{3-6}$ cycloalkyl
(i) —S(O)$_n$C$_{1-6}$alkyl,
(j) —S(O)$_2$aryl
(k) —S(O)$_2$ heterocycle
(l) —CO$_2$R$^8$,
(m) —SCF$_3$,
(n') a pyrrolidinyl, tetrahydrofuranyl, tetrahydrothienyl, piperidinyl, morpholinyl, thiomorpholinyl, dioxothiomorpholinyl and tetrahydropyranyl;

$R^8$ and $R^9$ are each independently selected from —H, $C_{1-6}$alkyl, pyrrolidinyl, tetrahydrofuranyl, tetrahydrothienyl, piperidinyl, morpholinyl, thiomorpholinyl, dioxothiomorpholinyl and tetrahydropyranyl;

Ra is selected from H, —NH$_2$, —NH(C$_1$-C$_6$)alkyl, —NR$^{10}$R$^{11}$, —NH—C(O)C$_1$-C$_6$alkyl, NR$^{11}$—C(O)C$_1$-C$_6$alkyl, —O(C$_1$-C$_8$)alkyl, —O(C$_3$-C$_6$)cycloalkyl, —S—(C$_1$-C$_6$)alkyl, —S(O)—C$_1$-C$_6$alkyl, —S(O)$_2$—C$_1$-C$_6$alkyl, and —CH$_2$—OH;

Rb is selected from —H, —(C$_1$-C$_6$)alkyl, —O—(C$_1$-C$_6$) alkyl, —NH$_2$, —CH$_2$—OH, —C≡N, —CH$_2$NH$_2$ and —C(O)OCH$_3$;

Rc is selected from —H, —CH$_3$ and, —OH;

$R^{10}$ and $R^{11}$ are each independently selected from —H, $C_{1-6}$alkyl, $C_{1-6}$alkyl-5-6 membered heterocyclyl, $C_{1-6}$alkyl-fluoropyridine and $C_{1-6}$alkyl-phenyll;

n is 0, 1 or 2.

In third embodiment, the present invention relates to a compound of formula (IB) as described in any of the preceding embodiments, wherein:
$R^1$ is selected from:

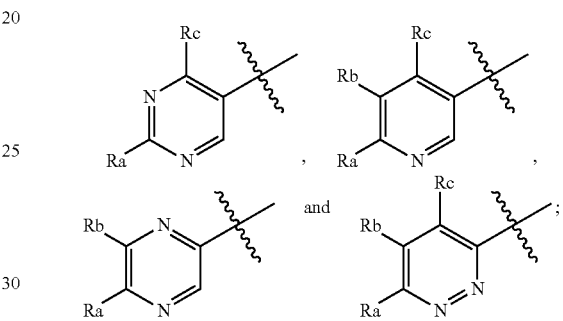

Ra is selected from H, —NH$_2$, —NH(C$_1$-C$_6$)alkyl, —NR$^{10}$R$^{11}$, —NH—C(O)C$_1$-C$_6$alkyl, NR$^{11}$—C(O)C$_1$-C$_6$alkyl, —O(C$_1$-C$_8$)alkyl, —O(C$_3$-C$_6$)cycloalkyl, —S—(C$_1$-C$_6$)alkyl, —S(O)—C$_1$-C$_6$alkyl, —S(O)$_2$—C$_1$-C$_6$alkyl and —CH$_2$—OH;

Rb is selected from —H, —(C$_1$-C$_6$)alkyl, —O—(C$_1$-C$_6$) alkyl, —NH$_2$, —CH$_2$—OH, —C≡N, —CH$_2$NH$_2$ and —C(O)OCH$_3$;

Rc is selected from —H, —CH$_3$ and, —OH;

$R^{10}$ and $R^{11}$ are each independently selected from —H, $C_{1-6}$alkyl, $C_{1-6}$alkyl-5-6 membered heterocyclyl, $C_{1-6}$alkyl-fluoropyridine and $C_{1-6}$alkyl-phenyl;

or a pharmaceutically acceptable salt thereof.

In a fourth embodiment there is provided a compound of formula (IB) as described in any of the preceding embodiments above, wherein:
$R^2$ is methyl, ethyl, propyl, isopropyl, dimethylpropyl, butyl, t-butyl or isobutyl;

or a pharmaceutically acceptable salt thereof.

In a fifth embodiment there is provided a compound of formula (IB) as described in any of the preceding embodiments, wherein:
$R^3$ is H, —OH, halogen, —CN, $C_{1-6}$ alkoxy, —COOR$^8$, —C(O)NR$^8$R$^9$, pyrrolyl, furanyl, thienyl, imidazolyl, pyrazolyl, triazolyl, pyridinyl, pyrimidinyl, pyrazinyl or pyridazinyl, wherein the heteroaryl ring is optionally substituted with $C_{1-3}$ alkyl;

$R^5$, $R^6$ and $R^7$ are each independently selected from
(a) —H,
(b) —OH,
(c) halogen,
(d) —CN,
(e) —CF$_3$, (f) $C_{1-6}$alkyl optionally substituted with one to three —OH, fluorine, $C_{1-6}$alkoxyl —N(R$^8$)(R$^9$), or —C(O)N(R$^8$)(R$^9$), (g) $C_{3-6}$ cycloalkyl (h) $C_{1-6}$alkoxy optionally substituted with one to three —OH, fluorine, —OC$_{1-6}$alkyl, or —OC$_{3-6}$ cycloalkyl (i) —S(O)$_2$C$_{1-6}$alkyl, (j) —S(O)$_2$aryl (k) —S(O)$_2$ heterocycle (l) —CO$_2$R$^8$, (m) —SCF$_3$, (n') a pyrrolidinyl, tetrahydrofuranyl, tetrahydrothienyl, piperidinyl, morpholinyl, thiomorpholinyl, dioxothiomorpholinyl and tetrahydropyranyl;

R$^8$ and R$^9$ are each independently selected from —H, C$_{1-6}$alkyl, pyrrolidinyl, tetrahydrofuranyl, tetrahydrothienyl, piperidinyl, morpholinyl, thiomorpholinyl, dioxothiomorpholinyl and tetrahydropyranyl;

or a pharmaceutically acceptable salt thereof.

In a sixth embodiment there is provided a compound of formula (IB) as described in the first or second embodiment above, wherein:

R$^1$ is selcted from:

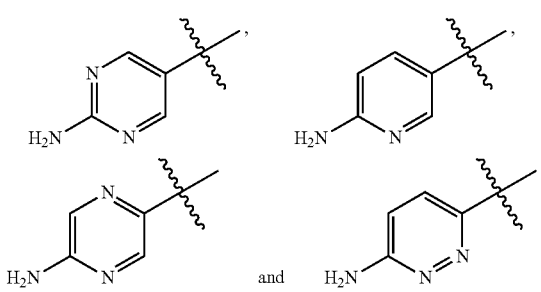

R$^2$ is t-butyl or dimethylpropyl;

R$^3$ is —H, C$_{1-3}$ alkoxy, or triazolyl which is optionally substituted with a methyl group;

R$^5$, R$^6$ and R$^7$ are each independently selected from (a) —H, (b) —OH, (c) halogen, (d) —CN, (e) —CF$_3$, (f) C$_{1-6}$alkyl optionally substituted with one to three —OH, fluorine, C$_{1-6}$alkoxyl —N(R$^8$)(R$^9$), or —C(O)N(R$^8$)(R$^9$), (g) C$_{3-6}$ cycloalkyl, (h) C$_{1-6}$alkoxy optionally substituted with one to three —OH, fluorine, —OC$_{1-6}$alkyl, or —OC$_{3-6}$ cycloalkyl, (i) morpholinyl or piperidinyl;

R$^8$ and R$^9$ are each independently selected from —H and C$_{1-6}$alkyl;

or a pharmaceutically acceptable salt thereof.

In a seventh embodiment there is provided a compound of formula (IB) as described in the sixth embodiment above, or a pharmaceutically acceptable salt thereof, wherein R$^1$ is

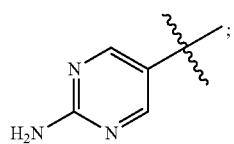 [SMILES: *c1cnc(N)nc1]

In an eighth embodiment there is provided a compound of formula (IB) as described in the sixth embodiment, wherein:

R$^2$ is t-butyl or dimethylpropyl;

or a pharmaceutically acceptable salt thereof.

In a ninth embodiment there is provided a compound of formula (IB) according to embodiment six, wherein:

R$^1$ is

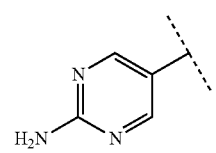

R$^2$ is t-butyl or dimethylpropyl;

R$^3$ is selected from

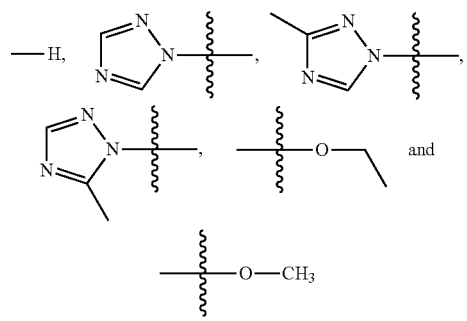

R$^5$, R$^6$ and R$^7$ are each independently selected from —H, —CN, F, Cl, Br, methyl, morpholinyl and methoxy;

or a pharmaceutically acceptable salt thereof.

In a tenth embodiment there is provided a compound of formula (IB) according to embodiment nine above, wherein:

R$^2$ is t-butyl;

R$^3$ is selected from

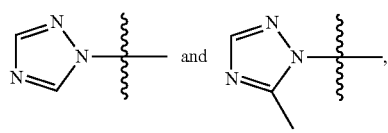

R$^5$, R$^6$ and R$^7$ are each independently selected from —H, methyl and Br;

or a pharmaceutically acceptable salt thereof.

In another first broadest embodiment, the present invention relates to a compound of formula IC wherein:
- R¹ is pyridinyl, pyrimidinyl, pyrazinyl, pyridazinyl, pyrrolopyridinyl, imidazopyridinyl, pyrazolopyridinyl or dihydropyrrolopyridinyl optionally substituted with oxo, wherein each heterocycle is optionally independently substituted with one to three groups selected from Ra, Rb and Rc;
- R² is $C_1$-$C_6$ alkyl or $C_{3-6}$ cycloalkyl optionally substituted with $C_{1-3}$ alkyl;
- R³ is H, —OH, halogen, —CN, $C_{1-6}$ alkoxy, —COOR⁸, —C(O)NR⁸R⁹ or 5-6 membered heteroaryl ring which is optionally substituted with $C_{1-3}$ alkyl;
- R⁴, R⁶, and R⁷ are each independently selected from
    - (a) —H,
    - (b) —OH,
    - (c) halogen,
    - (d) —CN,
    - (e) —CF₃,
    - (f) $C_{1-6}$alkyl optionally substituted with one to three —OH, fluorine, $C_{1-6}$alkoxyl —N(R⁸)(R⁹), or —C(O)N(R⁸)(R⁹),
    - (g) $C_{3-6}$ cycloalkyl
    - (h) $C_{1-6}$alkoxy optionally substituted with one to three —OH, fluorine, —O$C_{1-6}$alkyl, or —O$C_{3-6}$ cycloalkyl
    - (i) —S(O)$_n$$C_{1-6}$alkyl,
    - (j) —S(O)₂aryl
    - (k) —S(O)₂ heterocycle
    - (l) —CO₂R⁸,
    - (m) —SCF₃,
    - (n') a 5-6 membered heterocyclic ring;
- R⁸ and R⁹ are each independently selected from —H, $C_{1-6}$alkyl, and 5-6 membered heterocyclic ring;
- Ra is selected from H, —NH₂, —NH($C_1$-$C_6$)alkyl, —NR¹⁰R¹¹, —NH—C(O)$C_1$-$C_6$alkyl, NR¹¹—C(O)$C_1$-$C_6$alkyl, —O($C_1$-$C_8$)alkyl, —O($C_3$-$C_6$)cycloalkyl, —S—($C_1$-$C_6$)alkyl, —S(O)—$C_1$-$C_6$alkyl, —S(O)₂—$C_1$-$C_6$alkyl, and —CH₂—OH;
- Rb is selected from —H, —($C_1$-$C_6$)alkyl, —O—($C_1$-$C_6$) alkyl, —NH₂, —CH₂—OH, —C≡N, —CH₂NH₂ and —C(O)OCH₃;
- Rc is selected from —H, —CH₃ and, —OH;
- R¹⁰ and R¹¹ are each independently selected from —H, $C_{1-6}$alkyl, $C_{1-6}$alkyl-5-6 membered heterocyclyl, $C_{1-6}$alkyl-5-6 membered heteroaryl optionally substituted with halogen and $C_{1-6}$alkyl-aryl;
- n is 0, 1 or 2;

or a pharmaceutically acceptable salt thereof.

In a second embodiment, the present invention relates to a compound of formula (IC) as described in the broadest embodiment above, or a pharmaceutically acceptable salt thereof, wherein:

R¹ is selected from:

R² is methyl, ethyl, propyl, isopropyl, dimethylpropyl, butyl, t-butyl, isobutyl, pentyl, hexyl, cyclopropyl, cyclobutyl, cyclopentyl or cyclohexyl, wherein the cycloalkyl group is optionally substituted with a $C_{1-3}$ alkyl group;

R³ is H, —OH, halogen, —CN, $C_{1-6}$ alkoxy, —COOR⁸, —C(O)NR⁸R⁹, pyrrolyl, furanyl, thienyl, imidazolyl, pyrazolyl, triazolyl, pyridinyl, pyrimidinyl, pyrazinyl or pyridazinyl, wherein the heteroaryl ring is optionally substituted with $C_{1-3}$ alkyl;

R⁴, R⁶ and R⁷ are each independently selected from
- (a) —H,
- (b) —OH,
- (c) halogen,
- (d) —CN,
- (e) —CF₃,
- (f) $C_{1-6}$alkyl optionally substituted with one to three —OH, fluorine, $C_{1-6}$alkoxyl —N(R⁸)(R⁹), or —C(O)N(R⁸)(R⁹),
- (g) $C_{3-6}$ cycloalkyl
- (h) $C_{1-6}$alkoxy optionally substituted with one to three —OH, fluorine, —O$C_{1-6}$alkyl, or —O$C_{3-6}$ cycloalkyl
- (i) —S(O)$_n$$C_{1-6}$alkyl,
- (j) —S(O)₂aryl
- (k) —S(O)₂ heterocycle
- (l) —CO₂R⁸,
- (m) —SCF₃,
- (n') a pyrrolidinyl, tetrahydrofuranyl, tetrahydrothienyl, piperidinyl, morpholinyl, thiomorpholinyl, dioxothiomorpholinyl and tetrahydropyranyl;

R⁸ and R⁹ are each independently selected from —H, $C_{1-6}$alkyl, pyrrolidinyl, tetrahydrofuranyl, tetrahydrothienyl, piperidinyl, morpholinyl, thiomorpholinyl, dioxothiomorpholinyl and tetrahydropyranyl;

Ra is selected from H, —NH$_2$, —NH(C$_1$-C$_6$)alkyl, —NR$^{10}$R$^{11}$, —NH—C(O)C$_1$-C$_6$alkyl, NR$^{11}$—C(O)C$_1$-C$_6$alkyl, —O(C$_1$-C$_8$)alkyl, —O(C$_3$-C$_6$)cycloalkyl, —S—(C$_1$-C$_6$)alkyl, —S(O)—C$_1$-C$_6$alkyl, —S(O)$_2$—C$_1$-C$_6$alkyl, oxo and —CH$_2$—OH;

Rb is selected from —H, —(C$_1$-C$_6$)alkyl, —O—(C$_1$-C$_6$)alkyl, —NH$_2$, —CH$_2$—OH, —C≡N, —CH$_2$NH$_2$ and —C(O)OCH$_3$;

Rc is selected from —H, —CH$_3$ and, —OH;

R$^{10}$ and R$^{11}$ are each independently selected from —H, C$_{1-6}$alkyl, C$_{1-6}$alkyl-5-6 membered heterocyclyl, C$_{1-6}$alkyl-fluoropyridine and C$_{1-6}$alkyl-phenyl;

n is 0, 1 or 2.

In third embodiment, the present invention relates to a compound of formula (IC) as described in any of the preceding embodiments, wherein:

R$^1$ is selected from:

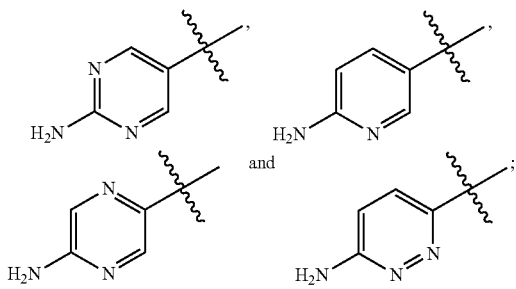

or a pharmaceutically acceptable salt thereof.

In a fourth embodiment there is provided a compound of formula (IC) as described in any of the preceding embodiments above, wherein:

R$^2$ is methyl, ethyl, propyl, isopropyl, dimethylpropyl, butyl, t-butyl or isobutyl;

or a pharmaceutically acceptable salt thereof.

In a fifth embodiment there is provided a compound of formula (IC) as described in any of the preceding embodiments, wherein:

R$^3$ is H, —OH, halogen, —CN, C$_{1-6}$ alkoxy, —COOR$^8$, —C(O)NR$^8$R$^9$, pyrrolyl, furanyl, thienyl, imidazolyl, pyrazolyl, triazolyl, pyridinyl, pyrimidinyl, pyrazinyl or pyridazinyl, wherein the heteroaryl ring is optionally substituted with C$_{1-3}$ alkyl;

R$^4$, R$^6$ and R$^7$ are each independently selected from
(a) —H,
(b) —OH,
(c) halogen,
(d) —CN,
(e) —CF$_3$,
(f) C$_{1-6}$alkyl optionally substituted with one to three —OH, fluorine, C$_{1-6}$alkoxyl —N(R$^8$)(R$^9$), or —C(O)N(R$^8$)(R$^9$),
(g) C$_{3-6}$ cycloalkyl
(h) C$_{1-6}$alkoxy optionally substituted with one to three —OH, fluorine, —OC$_{1-6}$alkyl, or —OC$_{3-6}$ cycloalkyl
(i) —S(O)$_2$C$_{1-6}$alkyl,
(j) —S(O)$_2$aryl
(k) -5 (O)$_2$ heterocycle
(l) —CO$_2$R$^8$,
(m) —SCF$_3$,
(n') a pyrrolidinyl, tetrahydrofuranyl, tetrahydrothienyl, piperidinyl, morpholinyl, thiomorpholinyl, dioxothiomorpholinyl and tetrahydropyranyl;

R$^8$ and R$^9$ are each independently selected from —H, C$_{1-6}$alkyl, pyrrolidinyl, tetrahydrofuranyl, tetrahydrothienyl, piperidinyl, morpholinyl, thiomorpholinyl, dioxothiomorpholinyl and tetrahydropyranyl;

or a pharmaceutically acceptable salt thereof.

In a sixth embodiment there is provided a compound of formula (IC) as described in the first or second embodiment above, wherein:

R$^1$ is selected from:

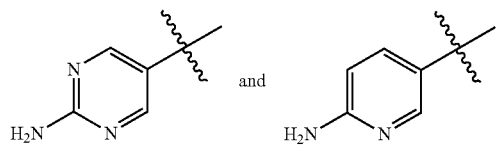 [SMILES: *c1cnc(N)nc1 ; *c1ccc(N)nc1]

R$^2$ is t-butyl;
R$^3$ is —H or halogen;
R$^4$, R$^6$ and R$^7$ are each independently selected from
(a) —H,
(b) —OH,
(c) halogen,
(d) —CN,
(e) —CF$_3$,
(f) C$_{1-6}$alkyl;
(g) C$_{3-6}$ cycloalkyl,
(h) C$_{1-6}$alkoxy optionally substituted with one to three —OH, fluorine, —OC$_{1-6}$alkyl, or —OC$_{3-6}$ cycloalkyl;
or a pharmaceutically acceptable salt thereof.

In a seventh embodiment there is provided a compound of formula (IC) as described in the sixth embodiment above, or a pharmaceutically acceptable salt thereof,
wherein R$^1$ is

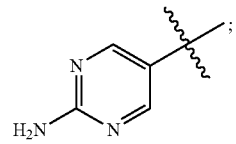

In an eighth embodiment there is provided a compound of formula (IC) as described in the sixth embodiment, wherein:
R$^2$ is t-butyl;
or a pharmaceutically acceptable salt thereof.

In a ninth embodiment there is provided a compound of formula (IC) according to embodiment six, wherein:
R$^1$ is

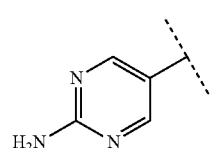

R$^2$ is t-butyl;
R$^3$ is F;
R$^4$, R$^6$ and Rare each independently selected from —H, Br and methoxy;
or a pharmaceutically acceptable salt thereof.

The following are representative compounds of the invention which can be made by the general synthetic schemes, the examples, and known methods in the art.

TABLE 1

| Example # | Structure | Name |
|---|---|---|
| 1 | 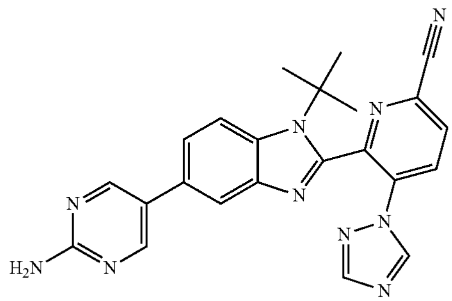 [SMILES: CC(C)(C)n1c(-c2nc(C#N)ccc2-n2cncn2)nc2cc(-c3cnc(N)nc3)ccc21] | 6-[5-(2-Amino-pyrimidin-5-yl)-1-tert-butyl-1H-benzimidazol-2-yl]-5-1,2,4-triazol-1-yl-pyridine-2-carbonitrile |
| 2 | 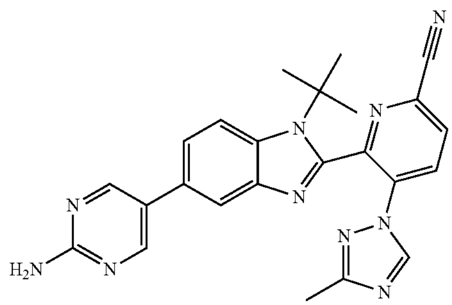 [SMILES: Cc1ncn(-c2ccc(C#N)nc2-c2nc3cc(-c4cnc(N)nc4)ccc3n2C(C)(C)C)n1] | 6-[5-(2-Amino-pyrimidin-5-yl)-1-tert-butyl-1H-benzimidazol-2-yl]-5-(3-methyl-1,2,4-triazol-1-yl)-pyridine-2-carbonitrile |
| 3 | 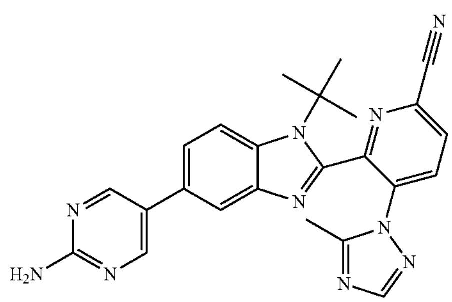 [SMILES: Cc1ncnn1-c1ccc(C#N)nc1-c1nc2cc(-c3cnc(N)nc3)ccc2n1C(C)(C)C] | 6-[5-(2-Amino-pyrimidin-5-yl)-1-tert-butyl-1H-benzimidazol-2-yl]-5-(5-methyl-1,2,4-triazol-1-yl)-pyridine-2-carbonitrile |
| 4 | 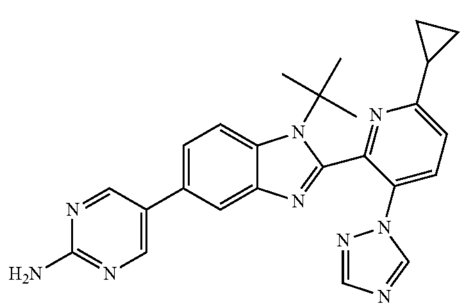 [SMILES: CC(C)(C)n1c(-c2nc(C3CC3)ccc2-n2cncn2)nc2cc(-c3cnc(N)nc3)ccc21] | 5-[1-tert-Butyl-2-(6-cyclopropyl-3-1,2,4-triazol-1-yl-pyridin-2-yl)-1H-benzimidazol-5-yl]-pyrimidin-2-ylamine |

TABLE 1-continued

| Example # | Structure | Name |
|---|---|---|
| 5 | 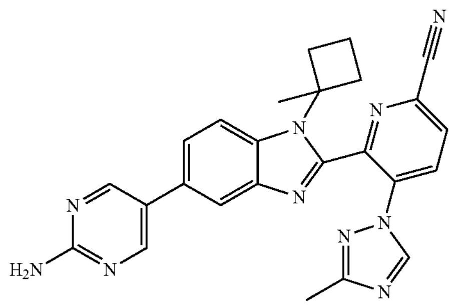 [SMILES: Cc1ncn(-c2ccc(C#N)nc2-c2nc3cc(-c4cnc(N)nc4)ccc3n2C2(C)CCC2)n1] | 6-[5-(2-Amino-pyrimidin-5-yl)-1-(1-methyl-cyclobutyl)-1H-benzimidazol-2-yl]-5-(3-methyl-1,2,4-triazol-1-yl)-pyridine-2-carbonitrile |
| 6 | 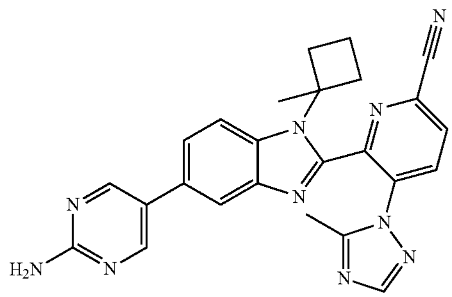 [SMILES: Cc1ncnn1-c1ccc(C#N)nc1-c1nc2cc(-c3cnc(N)nc3)ccc2n1C1(C)CCC1] | 6-[5-(2-Amino-pyrimidin-5-yl)-1-(1-methyl-cyclobutyl)-1H-benzimidazol-2-yl]-5-(5-methyl-1,2,4-triazol-1-yl)-pyridine-2-carbonitrile |
| 7 | 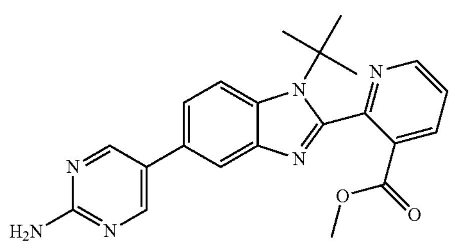 [SMILES: COC(=O)c1cccnc1-c1nc2cc(-c3cnc(N)nc3)ccc2n1C(C)(C)C] | 2-[5-(2-Amino-pyrimidin-5-yl)-1-tert-butyl-1H-benzimidazol-2-yl]-nicotinic acid methyl ester |
| 8 | 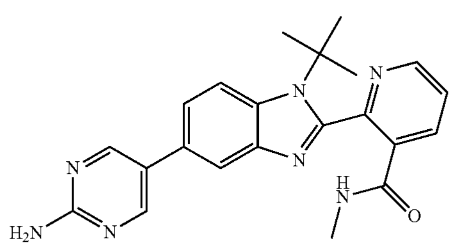 | 2-[5-(2-Amino-pyrimidin-5-yl)-1-tert-butyl-1H-benzimidazol-2-yl]-N-methyl-nicotinamide |
| 9 | 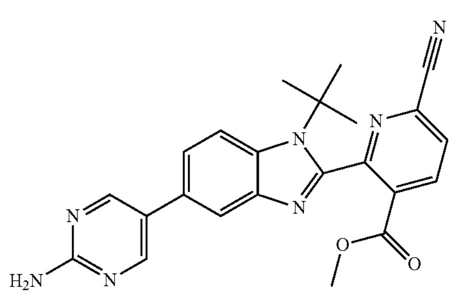 | 2-[5-(2-Amino-pyrimidin-5-yl)-1-tert-butyl-1H-benzimidazol-2-yl]-6-cyano-nicotinic acid methyl ester |

TABLE 1-continued

| Example # | Structure | Name |
|---|---|---|
| 10 | 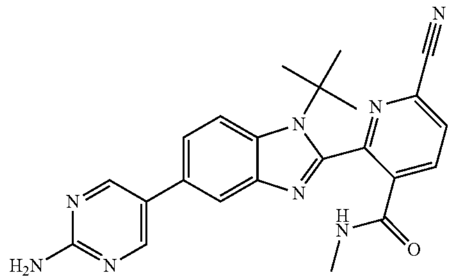 [SMILES: CNC(=O)c1ccc(C#N)nc1-c1nc2cc(-c3cnc(N)nc3)ccc2n1C(C)(C)C] | 2-[5-(2-Amino-pyrimidin-5-yl)-1-tert-butyl-1H-benzimidazol-2-yl]-6-cyano-N-methyl-nicotinamide |
| 11 | 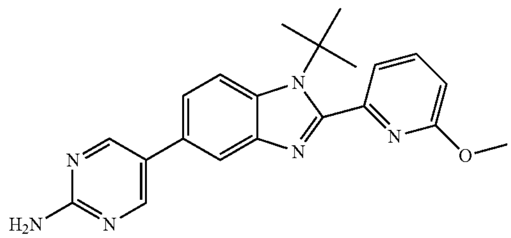 [SMILES: COc1cccc(-c2nc3cc(-c4cnc(N)nc4)ccc3n2C(C)(C)C)n1] | 5-[1-tert-Butyl-2-(6-methoxy-pyridin-2-yl)-1H-benzimidazol-5-yl]-pyrimidin-2-ylamine |
| 12 | 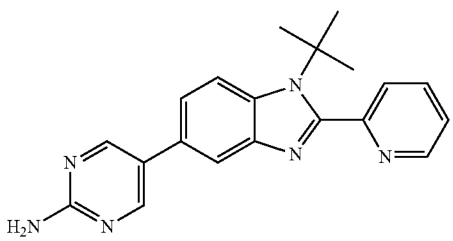 | 5-(1-tert-Butyl-2-pyridin-2-yl-1H-benzimidazol-5-yl)-pyrimidin-2-ylamine |
| 13 | 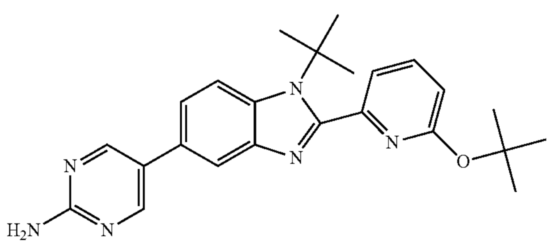 [SMILES: CC(C)(C)Oc1cccc(-c2nc3cc(-c4cnc(N)nc4)ccc3n2C(C)(C)C)n1] | 5-[2-(6-tert-Butoxy-pyridin-2-yl)-1-tert-butyl-1H-benzimidazol-5-yl]-pyrimidin-2-ylamine |
| 14 | 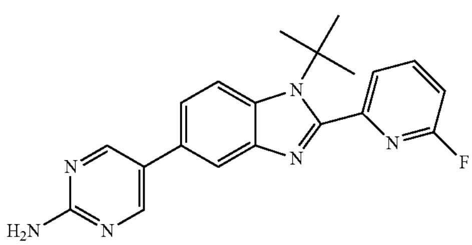 [SMILES: CC(C)(C)n1c(-c2cccc(F)n2)nc2cc(-c3cnc(N)nc3)ccc21] | 5-[1-tert-Butyl-2-(6-fluoro-pyridin-2-yl)-1H-benzimidazol-5-yl]-pyrimidin-2-ylamine |
| 15 | 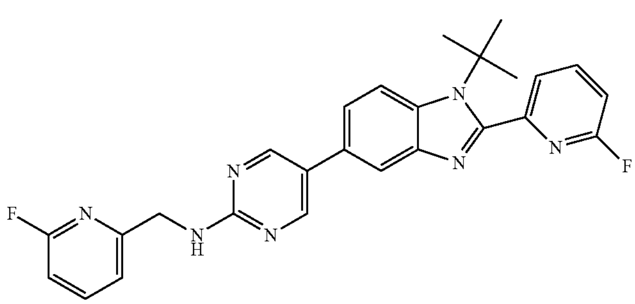 [SMILES: CC(C)(C)n1c(-c2cccc(F)n2)nc2cc(-c3cnc(NCc4cccc(F)n4)nc3)ccc21] | {5-[1-tert-Butyl-2-(6-fluoro-pyridin-2-yl)-1H-benzimidazol-5-yl]-pyrimidin-2-yl}-(6-fluoro-pyridin-2-ylmethyl)-amine |

TABLE 1-continued

| Example # | Structure | Name |
|---|---|---|
| 16 | 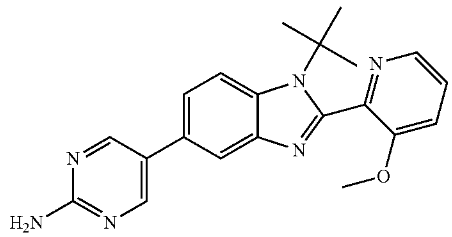 | 5-[1-tert-Butyl-2-(3-methoxy-pyridin-2-yl)-1H-benzimidazol-5-yl]-pyrimidin-2-ylamine |
| 17 | 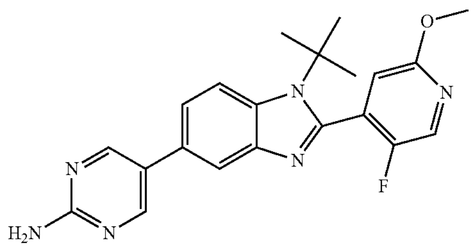 [SMILES: COc1cc(-c2nc3cc(-c4cnc(N)nc4)ccc3n2C(C)(C)C)c(F)cn1] | 5-[1-tert-Butyl-2-(5-fluoro-2-methoxy-pyridin-4-yl)-1H-benzimidazol-5-yl]-pyrimidin-2-ylamine |
| 18 | 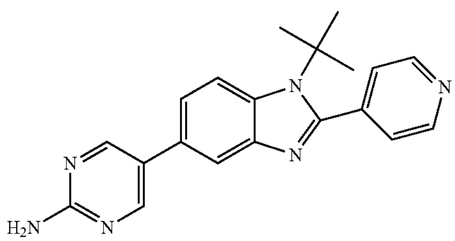 [SMILES: CC(C)(C)n1c(-c2ccncc2)nc2cc(-c3cnc(N)nc3)ccc21] | 5-(1-tert-Butyl-2-pyridin-4-yl-1H-benzimidazol-5-yl)-pyrimidin-2-ylamine |
| 19 | 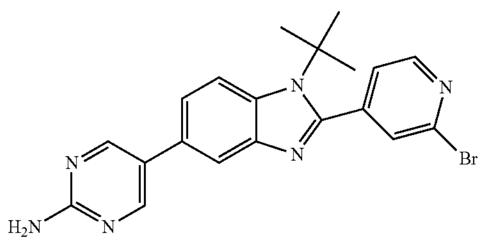 [SMILES: CC(C)(C)n1c(-c2ccnc(Br)c2)nc2cc(-c3cnc(N)nc3)ccc21] | 5-[2-(2-Bromo-pyridin-4-yl)-1-tert-butyl-1H-benzimidazol-5-yl]-pyrimidin-2-ylamine |
| 20 | 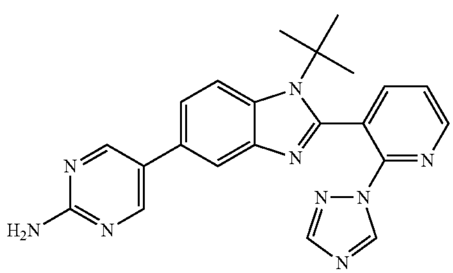 [SMILES: CC(C)(C)n1c(-c2cccnc2-n2cncn2)nc2cc(-c3cnc(N)nc3)ccc21] | 5-[1-tert-Butyl-2-(2-1,2,4-triazol-1-yl-pyridin-3-yl)-1H-benzimidazol-5-yl]-pyrimidin-2-ylamine |
| 21 | 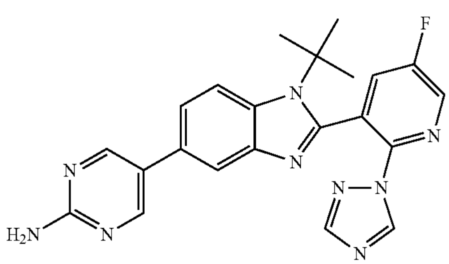 | 5-[1-tert-Butyl-2-(5-fluoro-2-1,2,4-triazol-1-yl-pyridin-3-yl)-1H-benzimidazol-5-yl]-pyrimidin-2-ylamine |

TABLE 1-continued

| Example # | Structure | Name |
|---|---|---|
| 22 | 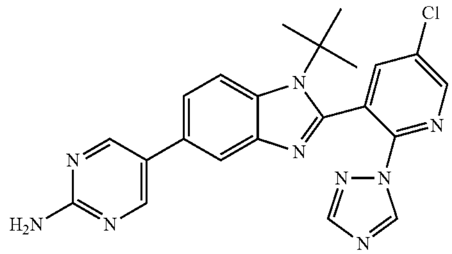 [SMILES: CC(C)(C)n1c(-c2cc(Cl)cnc2-n2cncn2)nc2cc(-c3cnc(N)nc3)ccc21] | 5-[1-tert-Butyl-2-(5-chloro-2-1,2,4-triazol-1-yl-pyridin-3-yl)-1H-benzimidazol-5-yl]-pyrimidin-2-ylamine |
| 23 | 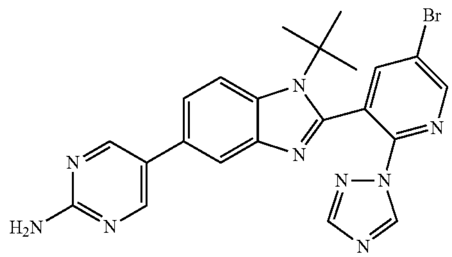 [SMILES: CC(C)(C)n1c(-c2cc(Br)cnc2-n2cncn2)nc2cc(-c3cnc(N)nc3)ccc21] | 5-[2-(5-Bromo-2-1,2,4-triazol-1-yl-pyridin-3-yl)-1-tert-butyl-1H-benzimidazol-5-yl]-pyrimidin-2-ylamine |
| 24 | 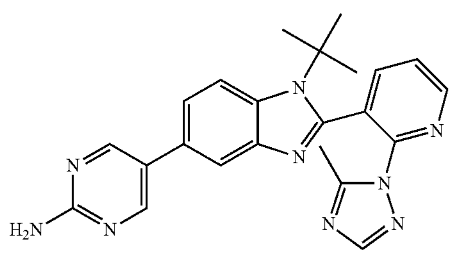 [SMILES: Cc1ncnn1-c1ncccc1-c1nc2cc(-c3cnc(N)nc3)ccc2n1C(C)(C)C] | 5-{1-tert-Butyl-2-[2-(5-methyl-1,2,4-triazol-1-yl)-pyridin-3-yl]-1H-benzimidazol-5-yl}-pyrimidin-2-ylamine |
| 25 | 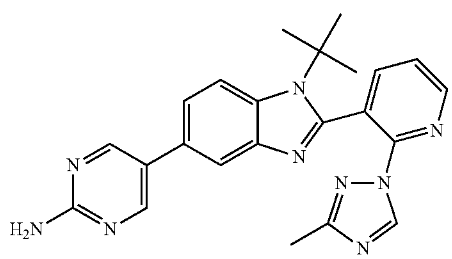 [SMILES: Cc1ncn(-c2ncccc2-c2nc3cc(-c4cnc(N)nc4)ccc3n2C(C)(C)C)n1] | 5-{1-tert-Butyl-2-[2-(3-methyl-1,2,4-triazol-1-yl)-pyridin-3-yl]-1H-benzimidazol-5-yl}-pyrimidin-2-ylamine |
| 26 | 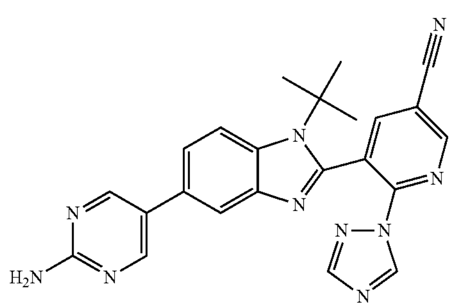 [SMILES: CC(C)(C)n1c(-c2cc(C#N)cnc2-n2cncn2)nc2cc(-c3cnc(N)nc3)ccc21] | 5-[5-(2-Amino-pyrimidin-5-yl)-1-tert-butyl-1H-benzimidazol-2-yl]-6-1,2,4-triazol-1-yl-nicotinonitrile |
| 27 | 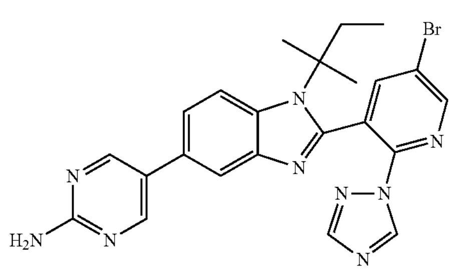 | 5-[2-(5-Bromo-2-1,2,4-triazol-1-yl-pyridin-3-yl)-1-(1,1-dimethyl-propyl)-1H-benzimidazol-5-yl]-pyrimidin-2-ylamine |

TABLE 1-continued

| Example # | Structure | Name |
|---|---|---|
| 28 | 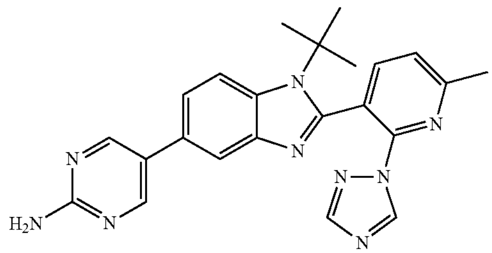 [SMILES: Cc1ccc(-c2nc3cc(-c4cnc(N)nc4)ccc3n2C(C)(C)C)c(-n2cncn2)n1] | 5-[1-tert-Butyl-2-(6-methyl-2-1,2,4-triazol-1-yl-pyridin-3-yl)-1H-benzimidazol-5-yl]-pyrimidin-2-ylamine |
| 29 | 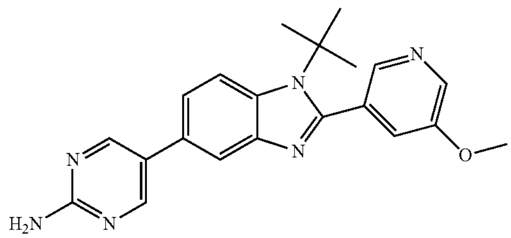 [SMILES: COc1cncc(-c2nc3cc(-c4cnc(N)nc4)ccc3n2C(C)(C)C)c1] | 5-[1-tert-Butyl-2-(5-methoxy-pyridin-3-yl)-1H-benzimidazol-5-yl]-pyrimidin-2-ylamine |
| 30 | 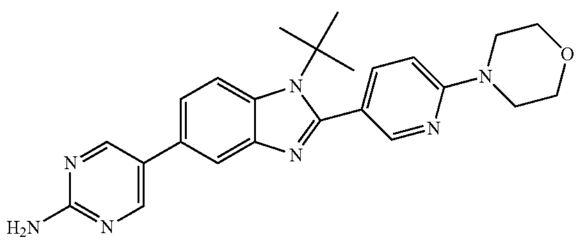 [SMILES: CC(C)(C)n1c(-c2ccc(N3CCOCC3)nc2)nc2cc(-c3cnc(N)nc3)ccc21] | 5-[1-tert-Butyl-2-(6-morpholin-4-yl-pyridin-3-yl)-1H-benzimidazol-5-yl]-pyrimidin-2-ylamine |
| 31 | 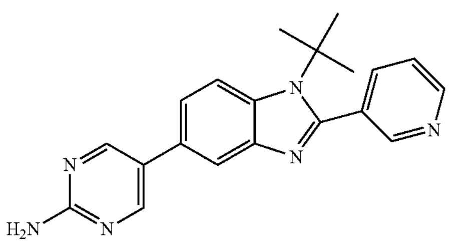 [SMILES: CC(C)(C)n1c(-c2cccnc2)nc2cc(-c3cnc(N)nc3)ccc21] | 5-(1-tert-Butyl-2-pyridin-3-yl-1H-benzimidazol-5-yl)-pyrimidin-2-ylamine |
| 32 | 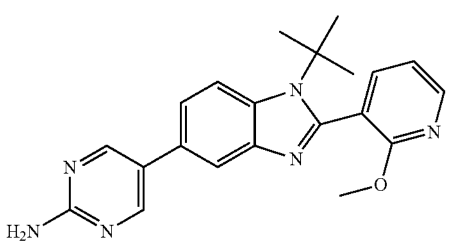 [SMILES: COc1ncccc1-c1nc2cc(-c3cnc(N)nc3)ccc2n1C(C)(C)C] | 5-[1-tert-Butyl-2-(2-methoxy-pyridin-3-yl)-1H-benzimidazol-5-yl]-pyrimidin-2-ylamine |
| 33 | 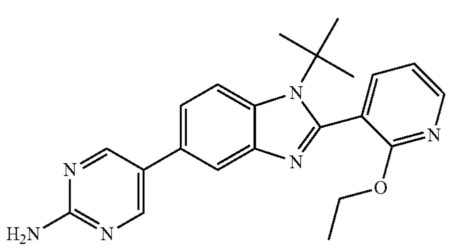 | 5-[1-tert-Butyl-2-(2-ethoxy-pyridin-3-yl)-1H-benzimidazol-5-yl]-pyrimidin-2-ylamine |

In one embodiment, the invention relates to any of the compounds depicted in Table 1 above and the pharmaceutically acceptable salts thereof.

Representative compounds of the invention show activity in the FLAP binding assay and in the human whole blood $LTB_4$ production inhibition assay, described in the assessment of biological properties section, as shown in Table 2.

TABLE 2

| Example# | hFLAP binding $IC_{50}$ (nM) | hWB $IC_{50}$ (nM) |
|---|---|---|
| 1 | 7.1 | 30 |
| 2 | 4.2 | 36 |
| 3 | 5.9 | 89 |
| 4 | 13 | 140 |
| 5 | 29 | 256 |
| 6 | 86 | 894 |
| 7 | 540 | 3096 |
| 8 | 620 | 1703 |
| 9 | 110 | 387 |
| 10 | 138 | 422 |
| 11 | 46 | |
| 12 | 700 | |
| 13 | 51 | |
| 14 | 279 | |
| 15 | 870 | |
| 16 | 960 | |
| 17 | 58 | 58 |
| 18 | 450 | 449 |
| 19 | 270 | 270 |
| 20 | 19 | 447 |
| 21 | 20 | 253 |
| 22 | 3.2 | 116 |
| 23 | 4.0 | 81 |
| 24 | 23 | 242 |
| 25 | 12 | 278 |
| 26 | 10 | 75 |
| 27 | 23 | 667 |
| 28 | 17 | 194 |
| 29 | 300 | |
| 30 | 180 | |
| 31 | 542 | |
| 32 | 220 | |
| 33 | 34 | |

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form.

The invention includes methods using all such tautomers.

All terms as used herein in this specification, unless otherwise stated, shall be understood in their ordinary meaning as known in the art. For example, "$C_{1-6}$ alkoxy" is a $C_{1-6}$ alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom. "Alkanoyl" refers to an alkyl group linked to a carbonyl group (C=O).

In all alkyl groups or carbon chains, one or more carbon atoms can be optionally replaced by heteroatoms such as O, S or N. It shall be understood that if N is not substituted then it is NH. It shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo. As used herein, "nitrogen" and "sulfur" include any oxidized form of nitrogen and sulfur and the quaternized form of any basic nitrogen. For example, for a —S—$C_{1-6}$ alkyl radical, unless otherwise specified, shall be understood to include —S(O)—$C_{1-6}$ alkyl and —S(O)$_2$—$C_{1-6}$ alkyl.

The term "$C_{3-10}$ carbocycle" or "cycloloalkyl" refers to a nonaromatic 3 to 10-membered (but preferably, 3 to 6-membered) monocyclic carbocyclic radical or a nonaromatic 6 to 10-membered fused bicyclic, bridged bicyclic, or spirocyclic carbocyclic radical. The $C_{3-10}$ carbocycle may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[3.3.0]octane, bicyclo[4.3.0]nonane, and bicyclo[4.4.0]decanyl (decahydronaphthalenyl). Non-limiting examples of 6 to 10-membered bridged bicyclic carbocyclic radicals include bicyclo [2.2.2]heptanyl, bicyclo [2.2.2]octanyl, and bicyclo[3.2.1]octanyl. Non-limiting examples of 6 to 10-membered spirocyclic carbocyclic radicals include but are not limited to spiro[3,3]heptanyl, spiro [3,4]octanyl and spiro[4,4]heptanyl.

The term "$C_{6-10}$ aryl" refers to aromatic hydrocarbon rings containing from six to ten carbon ring atoms. The term $C_{6-10}$ aryl includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

The term "5 to 11-membered heterocycle" refers to a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxothiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of non-aromatic 6 to 11-membered spirocyclic heterocyclic radicals include 7-aza-spiro[3,3]heptanyl, 7-spiro[3,4]octanyl, and 7-aza-spiro[3,4]octanyl.

The term "5 to 11-membered heteroaryl" shall be understood to mean an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S, Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include pyrrolopyridinyl, imidazopyridinyl, pyrazolopyridinyl, dihydropyrrolopyridinyl, benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl and benzothiazolyl.

It will be understood that one to three carbon ring moieties in the each of the $C_{3-10}$ carbocyclic rings, the 5 to 11-membered heterocyclic rings, the nonaromatic portion of the bicyclic aryl rings, and the nonaromatic portion of the bicyclic heteroaryl rings can independently be replaced with a carbonyl, thiocarbonyl, or iminyl moiety, i.e., —C(=O)—, —C(=S)— and —C(=NR$^8$)—, respectively, where R$^8$ is as defined above. The term "heteroatom" as used herein shall be understood to mean atoms other than carbon such as O, N, and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —CH$_2$CHF$_2$, —CF$_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula IA, IB or IC. A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$-$C_4$ alkyl)$_4$$^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula IA, IB or IC may be made using the general synthetic methods described below, which also constitute part of the invention.

General Synthetic Methods

The compounds of the invention may be prepared by the methods described below. In each of the schemes below, the groups R$^1$ to R$^7$ are as defined above for general formula IA, IB and IC, unless noted otherwise. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Typically, reaction progress may be monitored by thin layer chromatography (TLC) or HPLC-MS if desired. Intermediates and products may be purified by chromatography on silica gel, recrystallization, HPLC and/or reverse phase HPLC.

Starting materials and reagents are either commercially available or may be prepared by one skilled in the art using methods described in the chemical literature and in the Synthetic Examples section below.

Compounds of formula IA may be prepared as shown in Scheme 1.

Scheme 1

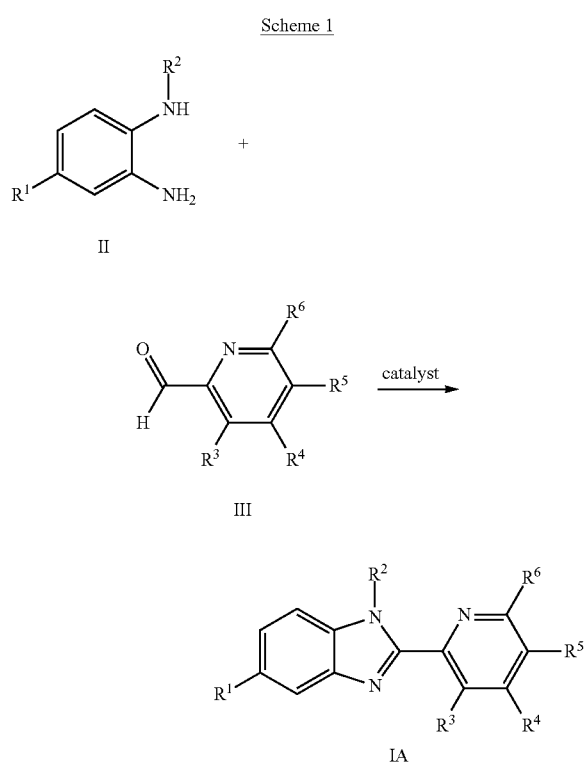

As illustrated in Scheme 1, a 1,2-diaminobenzene derivative substituted with $R^1$ and $R^2$ may be reacted with a pyridine aldehyde derivative substituted with $R^3$-$R^7$ to provide the desired compound of formula IA. The reaction may be run in acetic acid or in aqueous DMF in the presence of oxone or alternatively, in a suitable solvent such as methanol, in the presence of a suitable catalyst such as L-proline or p-toluenesulfonic acid.

Compounds of formula IB and IC may be prepared according to Scheme1, by using the corresponding 3 or 4 pyridine aldehyde.

Diamino intermediate II may be prepared as illustrated in Schemes 2

Scheme 2

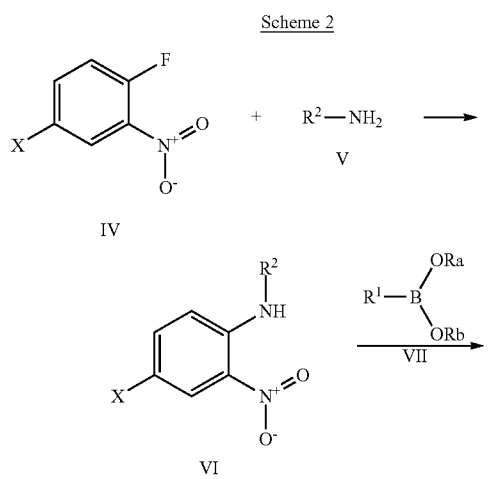

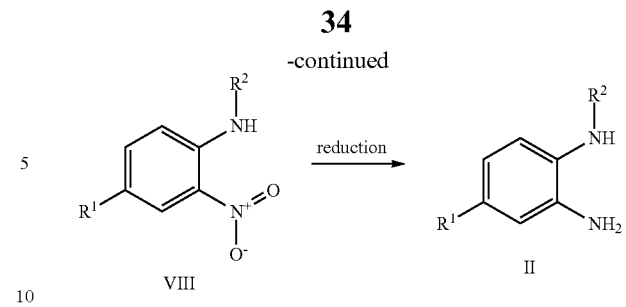

In Scheme 2, a disubstituted nitro benzene of formula IV, is reacted with an amine of formula V, in a suitable solvent, in the presence of a suitable base such as potassium carbonate, to provide an intermediate of formula VI. X is Cl or Br. Reaction of the intermediate of formula VI with a boronic acid ester of formula VII, in a suitable solvent, in the presence of a suitable catalyst, provides a coupled product of formula VIII. Ra and Rb are hydrogen or Ra and Rb together with the oxygen atoms to which they are attached form a 5-6 membered ring optionally substituted with 2-4 methyl groups. Reduction of nitro compound VIII provides an intermediate of formula II.

Intermediate III having $R^3$ being a nitrogen containing heteroaryl connected to the pyridine ring by the nitrogen, may be prepared as illustrated in Scheme 3.

Scheme 3

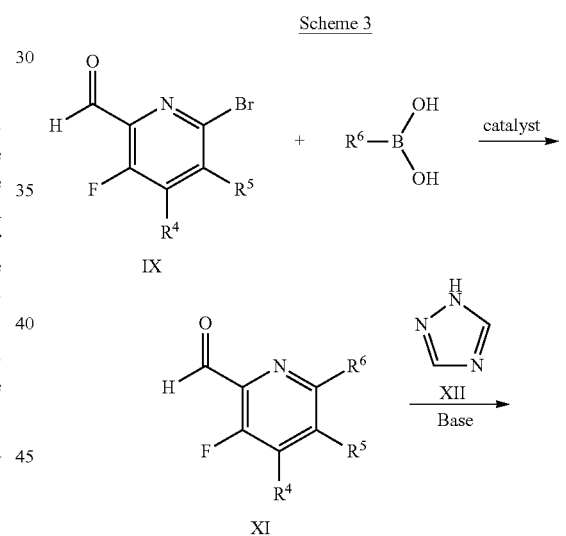

In Scheme 3, reaction of a substituted pyridine aldehyde of formula IX with a boronic acid of formula X or a boronic ester bearing $R^6$, in a suitable solvent, in the presence of a catalyst, provides an intermediate of formula XI. Compound of formula XI is reacted with a heteroaryl group having a NH in the ring, for example triazole XII, in the presence of a suitable base such as potassium carbonate in a suitable solvent such as DMSO to provide the desired intermediate of formula III ($R^3$=triazole).

Intermediate III may also be prepared according to Scheme 4.

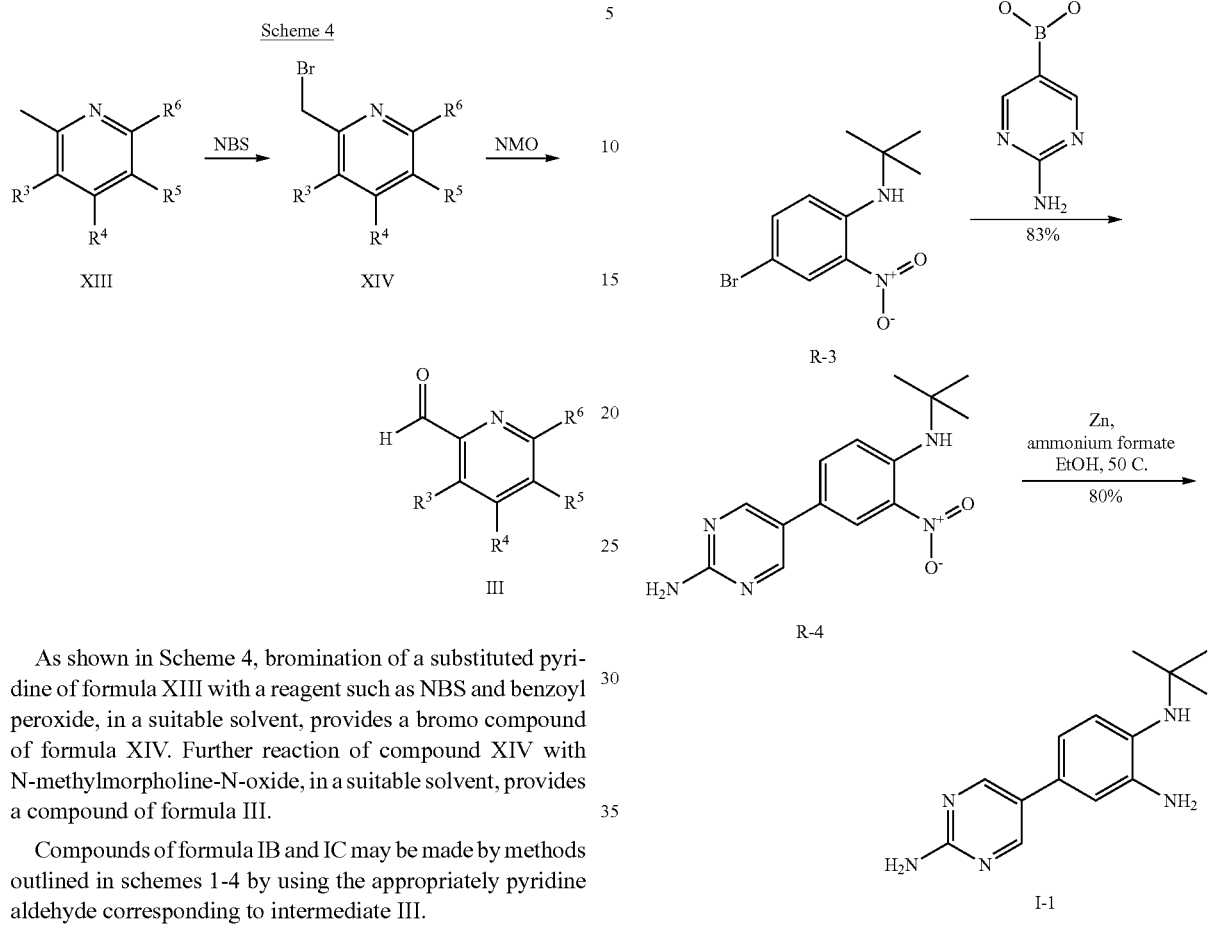

As shown in Scheme 4, bromination of a substituted pyridine of formula XIII with a reagent such as NBS and benzoyl peroxide, in a suitable solvent, provides a bromo compound of formula XIV. Further reaction of compound XIV with N-methylmorpholine-N-oxide, in a suitable solvent, provides a compound of formula III.

Compounds of formula IB and IC may be made by methods outlined in schemes 1-4 by using the appropriately pyridine aldehyde corresponding to intermediate III.

Compounds of formula IA, IB, IC as well as the respective intermediates prepared by the above methods may be further converted to additional intermediates or compounds of formula IA, IB and IC by methods known in the art and exemplified in the Synthetic Examples section below.

SYNTHETIC EXAMPLES

Synthesis of Intermediates 4-(2-Amino-pyrimidin-5-yl)-N-1-tert-butyl-benzene-1,2-diamine

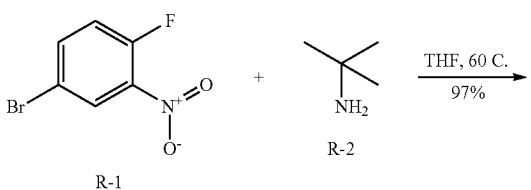

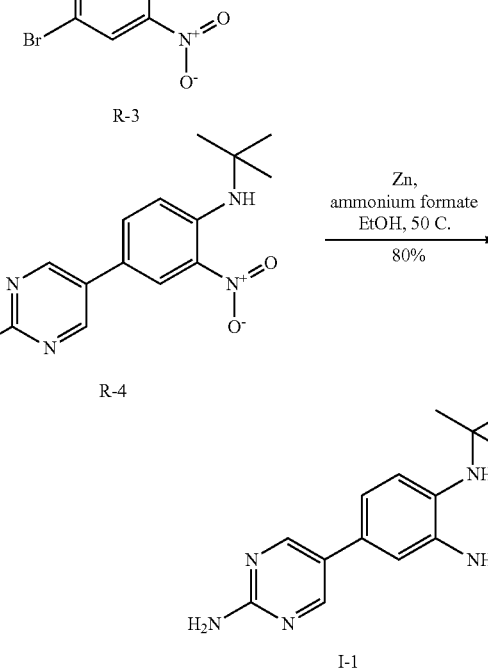

To a solution of R-1 (25 g, 0.1 mol) in THF (100 mL) is added R-2 (18 mL, 0.17 mol). The solution is heated at 60° C. for 16 hours. The solvent is removed in vacuum. The residue is suspended in methanol (20 mL). The precipitate is collected by filtration and washed with methanol to give R-3.

To a solution of R-3 (7.2 g, 0.026 mol) in DMF (100 mL) and $H_2O$ (10 mL) are added 5-(4,4,5,5-tetramethyl-1,3,2-dioxaborolan-2-yl)-pyrimidin-2-ylamine (8.7 g, 0.04 mol), $Pd(PPh_3)_4$ (3 g, 0.003 mol) and $K_2CO_3$ (7.3 g, 0.053 mol) at room temperature. The solution is heated to 100° C. for 2 hours. The solution is cooled down, washed with $H_2O$ (100 mL) and extracted with EtOAc. The combined organic layer is dried with $MgSO_4$ and filtered. The filtrate is concentrated and the residue is re-crystallized in $CH_2Cl_2$ to afford R-4.

To a round bottom flask are added R-4 (6.3 g, 0.02 mol) and ammonium formate (6.9 g, 0.1 mol) in EtOH, (100 mL), followed by the addition of zinc dust (4.3 g, 0.066 mol). The reaction mixture is stirred at 50° C. for 2 hours. The reaction mixture is filtered through a short pad of diatomaceous earth. The filter pad is rinsed with MeOH (50 mL) and the combined filtrate is concentrated. The residue is extracted with $H_2O$ (50 mL) and EtOAc (3×50 mL). The combined organic layer is washed with saturated $NaHCO_3$ solution, dried ($MgSO_4$) and filtered. The filtrate is concentrated to afford the title intermediate I-1 (4.5 g).

The following intermediates were synthesized in similar fashion from the appropriate reagents:

| Intermediate | Structure |
|---|---|
| I-2 | 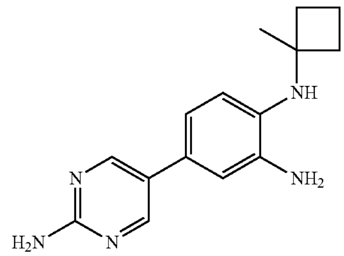 [SMILES: CC1(Nc2ccc(-c3cnc(N)nc3)cc2N)CCC1] |
| I-3 | 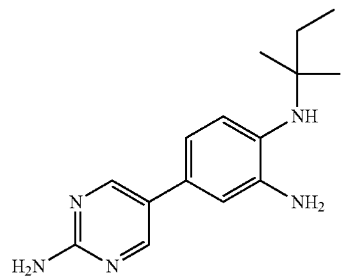 [SMILES: CCC(C)(C)Nc1ccc(-c2cnc(N)nc2)cc1N] |

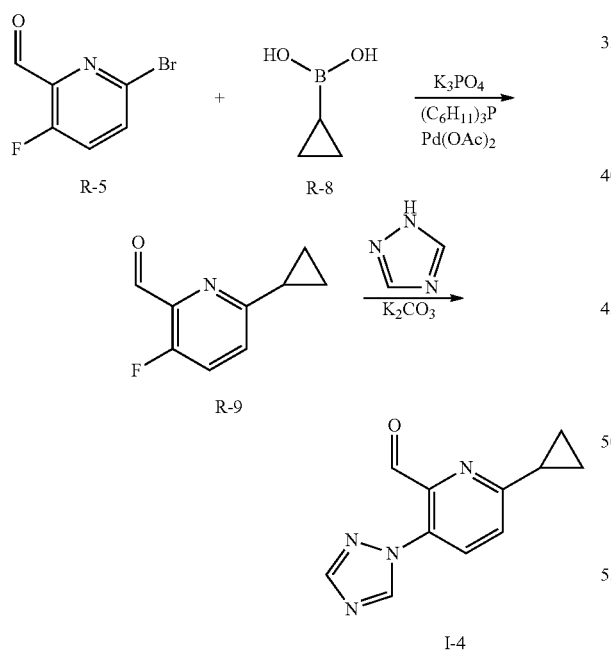

6-Cyclopropyl-3-1,2,4-triazol-1-yl-pyridine-2-carbaldehyde

R-5 (2.20 g, 10.78 mmol) is combined with R-8 (1.20 g, 14.02 mmol), tribasic potassium phosphate (8.01 g, 37.75 mmol) and tricyclohexylphosphine (0.30 g, 1.08 mmol) and diluted with toluene (40 ml) and water (2 ml). The palladium acetate is added (0.24 g, 1.08 mmol) and the mixture is sonicated for five minutes and then degassed with nitrogen. The reaction is warmed to 100° C. for 22 hours, cooled to ambient temperature and poured into water. The product is extracted into ethyl acetate and the organics are dried with MgSO$_4$, filtered and concentrated. The residue is purified by silica gel flash column chromatography with 5-40% ethyl acetate in heptane as the eluent to afford R-9. R-9 (250 mg, 1.51 mmol) in DMSO (10 ml) is treated with 1,2,4-triazole (125 mg, 1.82 mmol) and potassium carbonate (420 mg, 3.03 mmol). The resulting mixture is warmed to 80° C. for 5 minutes in a microwave reactor. The reaction is poured into water and the product is extracted into ethyl acetate. The combined organics are dried with MgSO$_4$, filtered and concentrated. The residue is purified by silica gel flash column chromatography with 5-100% ethyl acetate in heptane as the eluent to give the title intermediate 1-4 (175 mg).

6-Cyano-2-formyl-nicotinic acid methyl ester

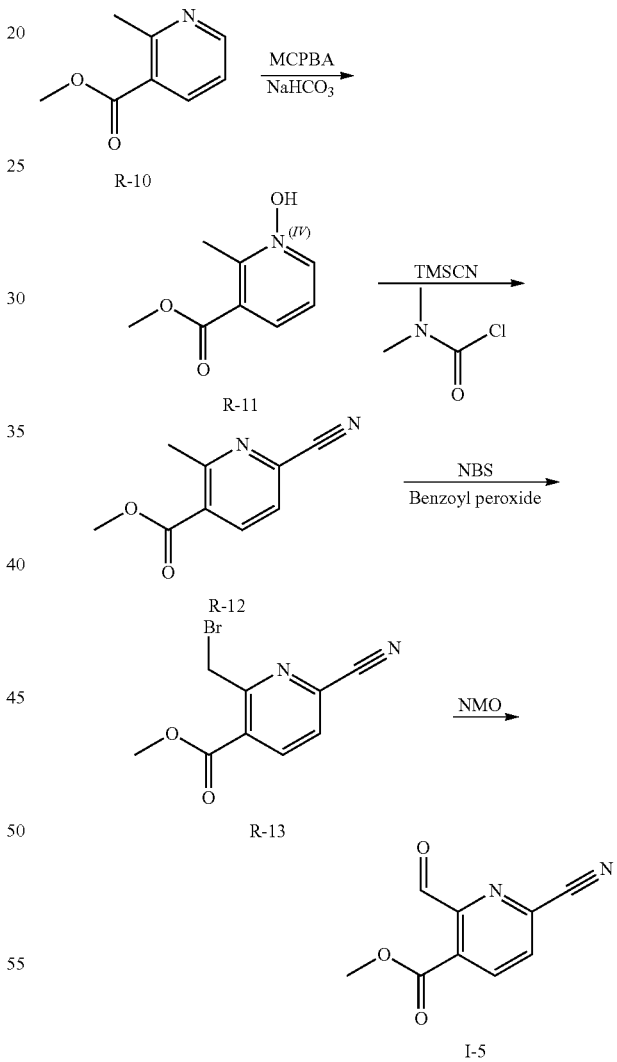

To a solution of R-10 (300 mg, 1.98 mmol) in CH$_2$Cl$_2$ (10 ml) is added mCPBA (890 mg, 3.97 mmol) at room temperature. The solution is stirred at the same temperature for 24 hours. The solution is filtered and the filtrate is concentrated. The residue is purifed by silica gel flash column chromatography with 10% MeOH in CH$_2$Cl$_2$ as the eluent to afford R-11 as a white solid.

To a solution of R-11 (527 mg, 3.13 mmol) in $CH_2Cl_2$ (10 ml) is added trimethylsilyl cyanide (622 mg, 6.27 mmol) and dimethylcarbamyl chloride (0.59 ml, 6.27 mmol) at room temperature. The solution is stirred at the same temperature for 48 hours. The solution is concentrated and the residue is purified by silica gel flash cloumn chromatography with 10% EtOAc in heptane as the eluent to afford R-12 as a colorless oil.

To a solution of R-12 (316 mg, 1.79 mmol) in $CCl_4$ (10 ml) is added N-bromosuccinimide (639 mg, 3.59 mmol) and benzoyl peroxide (869 mg, 3.59 mmol) at room temperature. The mixture is heated at 100° C. for 6 hours. The solution is cooled down and extracted with $CH_2Cl_2$ and $H_2O$. The combined organic layers are dried with $MgSO_4$ and filtered. The filtrate is concentrated and the residue purified by silica gel flash column chromatography with 10% EtOAc in Heptane as the eluent to afford R-13 as a pale brown foam.

To a solution of R-13 (700 mg, 2.74 mmol) in $CH_3CN$ (10 ml) is added N-methylmorpholine-N-oxide (649 mg, 5.49 mmol) at room temperature. The solution is stirred at the same temperature for 12 hours. The solution is concentrated and the residue purified by silica gel flash column chromatography with 10% EtOAc in Heptane as the eluent to afford 1-5 (500 mg) as an colorless oil.

2-Formyl-nicotinic acid methyl ester

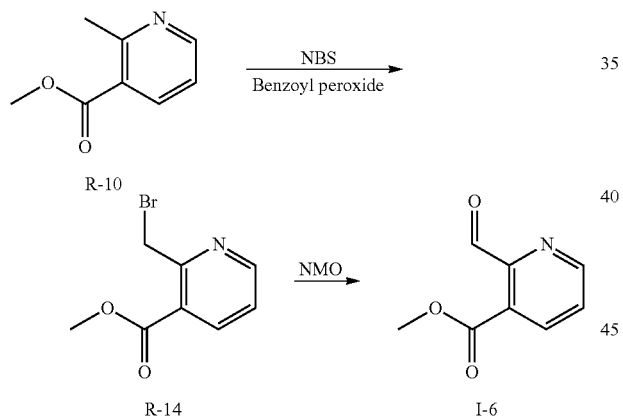

To a solution of R-10 (300 mg, 1.98 mmol) in $CCl_4$ (10 ml) is added N-bromosuccinimide (706 mg, 3.97 mmol) and benzoyl peroxide (720 mg, 2.98 mmol) at room temperature. The mixture is heated at 100° C. for 6 hours. The solution is cooled down and extracted with $CH_2Cl_2$ and $H_2O$. The combined organic layers are dried with $MgSO_4$ and filtered. The filtrate is concentrated and the residue purified by silica gel flash column chromatography with 10% EtOAc in Heptane as the eluent to afford R-14 as a pale brown foam.

To a solution of R-14 (214 mg, 0.93 mmol) in $CH_3CN$ (8 ml) is added N-methylmorpholine-N-oxide (220 mg, 1.86 mmol) at room temperature. The solution is stirred at the same temperature for 12 hours. The solution is concentrated and the residue purified by silica gel flash column chromatography with 10% EtOAc in Heptane as the eluent to afford 1-6 (140 mg) as an colorless oil.

2-1,2,4-Triazol-1-yl-pyridine-3-carbaldehyde

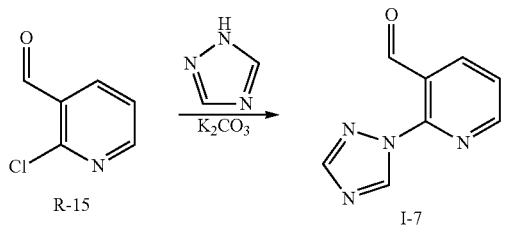

R-15 (200 mg, 1.41 mmol) and 1,2,4-triazole (127 mg, 1.84 mmol) are combined in DMF (5 ml) and warmed to 70° C. for 16 hours. The reaction is cooled to room temperature and poured into water. The product is extracted into EtOAc and the combined organics are dried ($MgSO_4$), filtered and concentrated to afford 1-7 (160 mg).

The following intermediates were synthesized in similar fashion from the appropriate reagents:

| Intermediate | Strucuture |
|---|---|
| I-8 | ![structure I-8] |
| I-9 | ![structure I-9] |
| I-10 | ![structure I-10] |
| I-11 | ![structure I-11] |

| Intermediate | Strucuture |
|---|---|
| I-12 | 6-Methyl-2-1,2,4-triazol-1-yl-pyridine-3-carbaldehyde |

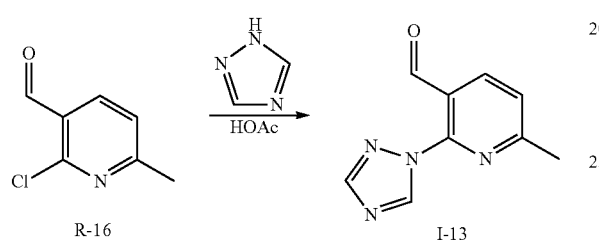

R-16 (1.00 g, 6.43 mmol) and 1,2,4-triazole (0.89 g, 12.86 mmol) are combined in HOAc (15 ml) and warmed to 118° C. After 3 hours the reaction is cooled to room temperature and concentrated. The residue is purified by silica gel flash column chromatography with 0-4% MeOH in CH$_2$Cl$_2$ as the eluent to afford I-13.

Synthesis of Final Compounds

Method 1

Synthesis of 6-[5-(2-Amino-pyrimidin-5-yl)-1-tert-butyl-1H-benzimidazol-2-yl]-5-(3-methyl-1,2,4-triazol-1-yl)-pyridine-2-carbonitrile (Example 2, Table 1)

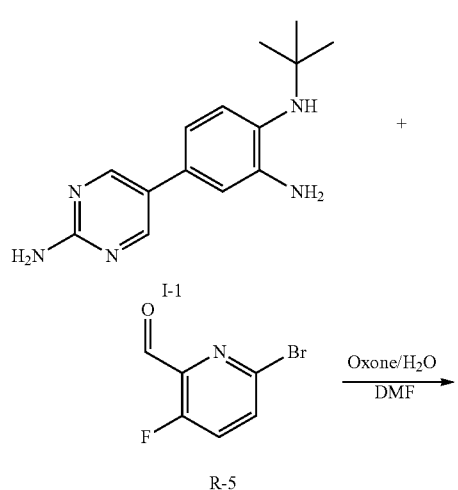

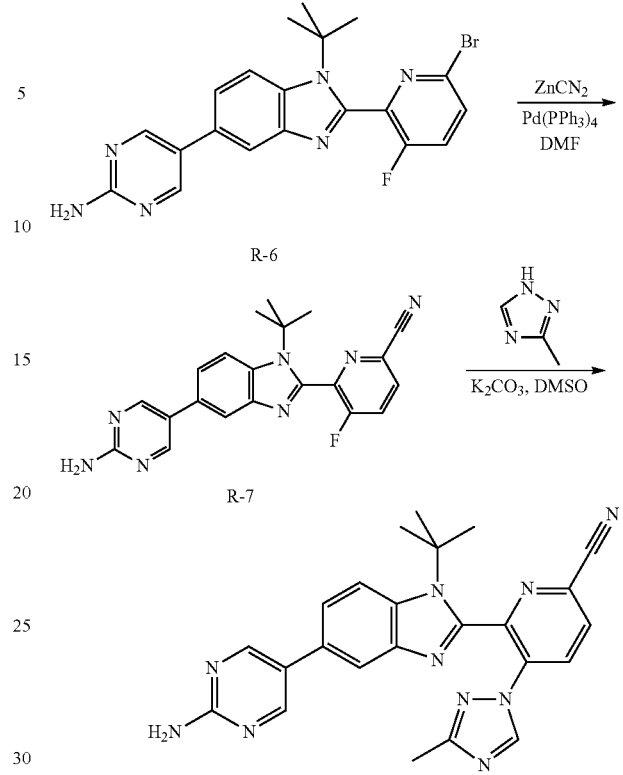

To a solution of I-1 (500 mg, 1.94 mmol) in DMF (20 mL) is added R-5 (396 mg, 1.94 mmol) followed by a solution of oxone (1.19 g, 1.94 mmol) in water (6 ml) at room temperature. The solution is stirred for 30 minutes and poured into water (75 ml) and saturated aqueous sodium thiosulfate (75 ml). The product is extracted into ethyl acetate and the organics are dried with MgSO$_4$, filtered and concentrated. The residue is purified by silica gel flash column chromatography with 10% MeOH in CH$_2$Cl$_2$ as the eluent to afford R-6.

R-6 (480 mg, 1.09 mmol) is dissolved in DMF (10 ml) and treated with zinc cyanide (130 mg, 1.09 mmol) and tetrakis(triphenylphosphine)palladium (0) (50 mg, 0.043 mmol). The reaction is degassed using nitrogen, heated at 175° C. in a microwave reactor for 3 minutes and poured into water. The product is extracted into ethyl acetate and the combined organics are dried over MgSO$_4$, filtered and concentrated. The residue is purified by silica gel flash column chromatography with 10% MeOH in CH$_2$Cl$_2$ as the eluent to afford R-7.

R-7 (300 mg, 0.77 mmol) in DMSO (5 ml) is treated with 3-methyl-1H-(1,2,4)-triazole (77 mg, 0.93 mmol) and potassium carbonate (210 mg, 1.55 mmol). The resulting mixture is warmed to 75° C. for 2 hours and cooled to ambient temperature. The reaction is poured into water and the product is extracted into ethyl acetate. The combined organics are dried with MgSO$_4$, filtered and concentrated. The residue is sequentially purified by silica gel flash column chromatography with 0-10% MeOH in CH$_2$Cl$_2$ as the eluent and reverse phase HPLC with 22% acetonitrile (0.1% TFA) in water (0.1% TFA) to give 2 (90 mg).

The following compounds were synthesized in similar fashion from the appropriate intermediates:
Example 1, Table 1
Example 3, Table 1
Example 5, Table 1
Example 6, Table 1

Method 2

Synthesis of 5-[1-tert-Butyl-2-(6-cyclopropyl-3-1,2,4-triazol-1-yl-pyridin-2-yl)-1H-benzimidazol-5-yl]-pyrimidin-2-ylamine (Example 4, Table 1)

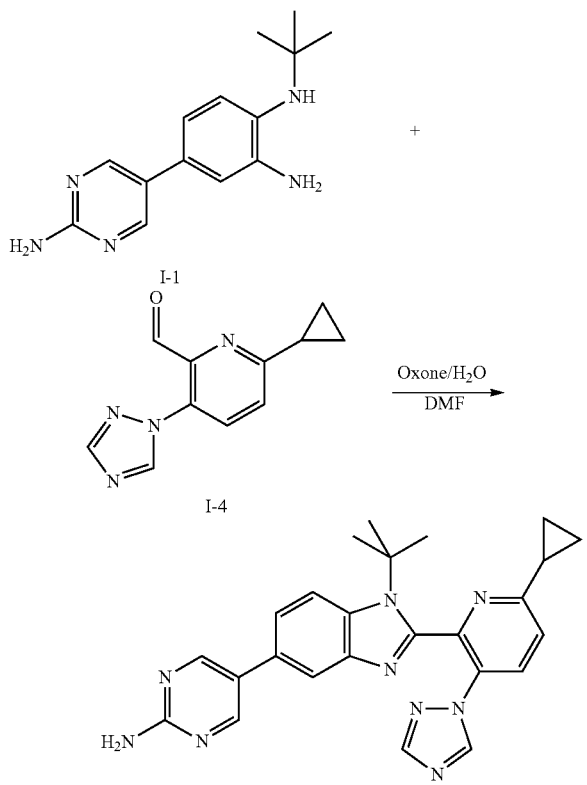

To a solution of I-1 (210 mg, 0.82 mmol) in DMF (10 mL) is added 1-4 (175 mg, 0.82 mmol) followed by a solution of oxone (500 mg, 0.82 mmol) in water (2 ml) at room temperature. The solution is stirred for 30 minutes and poured into water (40 ml) and saturated aqueous sodium thiosulfate (25 ml). The product is extracted into ethyl acetate and the organics are dried with $MgSO_4$, filtered and concentrated. The residue is purified by silica gel flash column chromatography with 0-10% MeOH in $CH_2Cl_2$ as the eluent to give 4 (175 mg).

The following compounds were synthesized in similar fashion from the appropriate intermediates:
Example 7, Table 1
Example 9, Table 1
Examples 11-19, Table 1
Example 23, Table 1
Example 29-33, Table 1

Method 3

Synthesis of 2-[5-(2-Amino-pyrimidin-5-yl)-1-tert-butyl-1H-benzimidazol-2-yl]-6-cyano-N-methyl-nicotinamide (Example 10, Table 1)

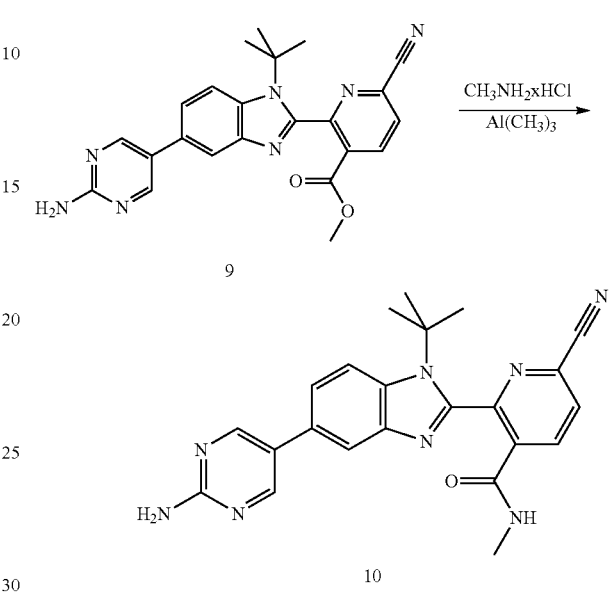

To a solution of methlyamine hydrochlorde (35 mg, 0.51 mmol) in dry toluene (10 ml) is added $AlMe_3$ (0.35 ml, 0.70 mmol) at room temperature. The solution is stirred at the same temperature for 15 minutes. 9 (100 mg, 0.23 mmol) in toluene is added to the solution and it is heated at 90° C. for 3 hours. The mixture is cooled down to room temperature and water is added. The mixture is extracted with EtOAc and the combined organic layers are dried by $MgSO_4$ and filtered. The filtrate is concentrated and the residue purified by silica gel flash column chromatography with 10% MeOH in $CH_2Cl_2$ as the eluent to afford 10 (10 mg) as a white foam.

The following compounds were synthesized in similar fashion from the appropriate intermediates:
Example 8, Table 1

Method 4

Synthesis of 5-[1-tert-Butyl-2-(5-chloro-2-1,2,4-triazol-1-yl-pyridin-3-yl)-1H-benzimidazol-5-yl]-pyrimidin-2-ylamine (Example 22, Table 1)

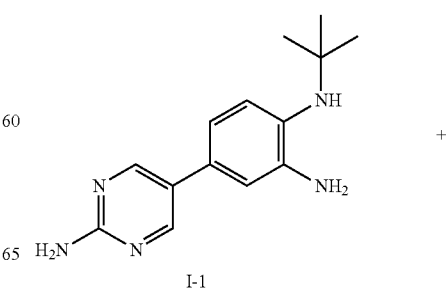

-continued

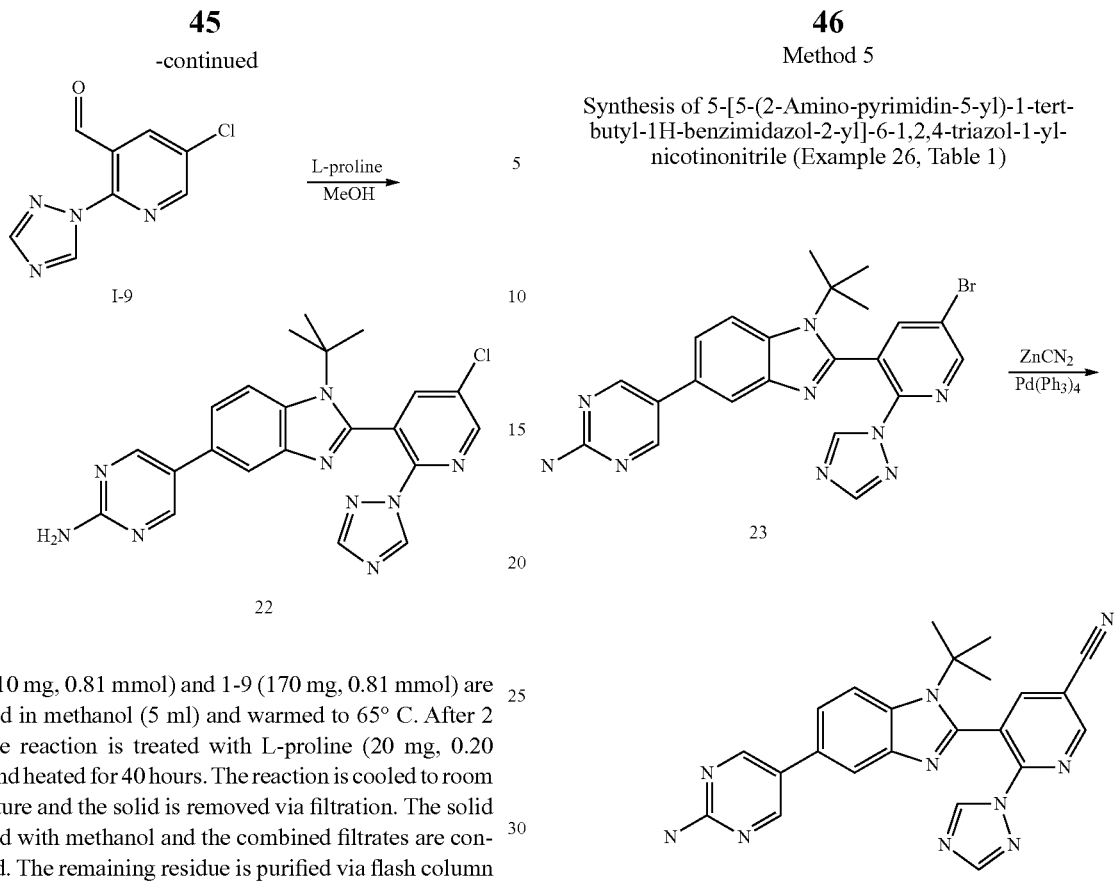

I-1 (210 mg, 0.81 mmol) and 1-9 (170 mg, 0.81 mmol) are combined in methanol (5 ml) and warmed to 65° C. After 2 hours the reaction is treated with L-proline (20 mg, 0.20 mmol) and heated for 40 hours. The reaction is cooled to room temperature and the solid is removed via filtration. The solid is washed with methanol and the combined filtrates are concentrated. The remaining residue is purified via flash column chromatography with 2-10% MeOH in $CH_2Cl_2$ as the eluent to afford 22 (70 mg).

The following compounds were synthesized in similar fashion from the appropriate intermediates:

Example 20, Table 1
Example 21, Table 1
Example 24, Table 1
Example 25, Table 1
Example 27, Table 1
Example 28, Table 1

Method 5

Synthesis of 5-[5-(2-Amino-pyrimidin-5-yl)-1-tert-butyl-1H-benzimidazol-2-yl]-6-1,2,4-triazol-1-yl-nicotinonitrile (Example 26, Table 1)

In a microwave reaction vessel is dissolved 23 (370 mg, 0.75 mmol) in DMF (5 ml). Zinc cyanide (89 mg, 0.75 mmol) is added, followed by the tetrakis (triphenylphosphine)palladium (0) (30 mg, 0.030 mmol). The reaction is degassed with nitrogen and heated to 175° C. in a microwave for 3 minutes. The reaction is poured into water and extracted with ethyl acetate. The combined organics are dried ($MgSO_4$), filtered and concentrated. The residue is purified by flash column chromatography with 2-10% MeOH in $CH_2Cl_2$ as the eluent to afford 26 (60 mg).

TABLE 3

Final Compounds

| Example # | Structure | Method | Retention time (min) | m/z [M + H]+ | LC/MS Method |
|---|---|---|---|---|---|
| 1 | 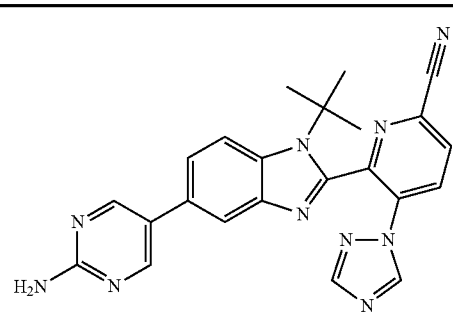 | 1 | 1.3 | 437.2 | A |

TABLE 3-continued

Final Compounds

| Example # | Structure | Method | Retention time (min) | m/z [M + H]+ | LC/MS Method |
|---|---|---|---|---|---|
| 2 | 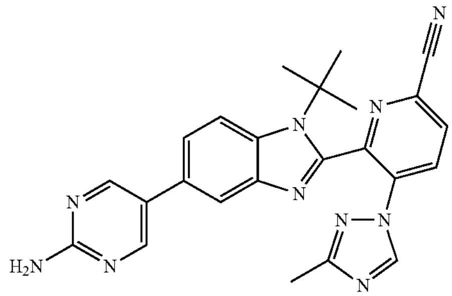 [SMILES: Cc1ncn(-c2ccc(C#N)nc2-c2nc3cc(-c4cnc(N)nc4)ccc3n2C(C)(C)C)n1] | 1 | 1.1 | 451.2 | B |
| 3 | 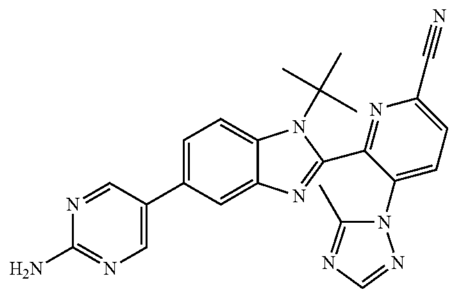 [SMILES: Cc1ncnn1-c1ccc(C#N)nc1-c1nc2cc(-c3cnc(N)nc3)ccc2n1C(C)(C)C] | 1 | 1.1 | 451.2 | B |
| 4 | 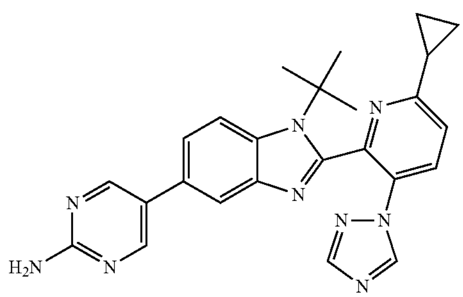 [SMILES: CC(C)(C)n1c(-c2nc(C3CC3)ccc2-n2cncn2)nc2cc(-c3cnc(N)nc3)ccc21] | 2 | 1.3 | 452.4 | C |
| 5 | 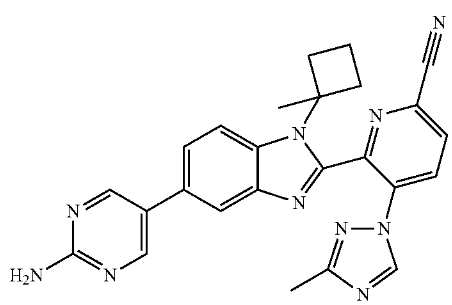 [SMILES: Cc1ncn(-c2ccc(C#N)nc2-c2nc3cc(-c4cnc(N)nc4)ccc3n2C2(C)CCC2)n1] | 1 | 1.4 | 463.4 | A |
| 6 | 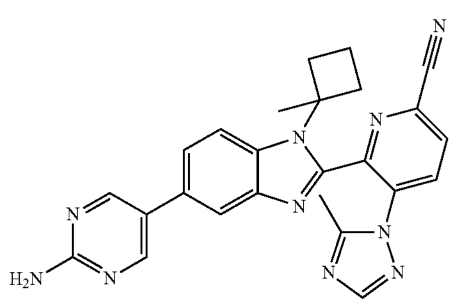 [SMILES: Cc1ncnn1-c1ccc(C#N)nc1-c1nc2cc(-c3cnc(N)nc3)ccc2n1C1(C)CCC1] | 1 | 0.9 | 463.2 | E |

TABLE 3-continued

Final Compounds

| Example # | Structure | Method | Retention time (min) | m/z [M + H]+ | LC/MS Method |
|---|---|---|---|---|---|
| 7 | 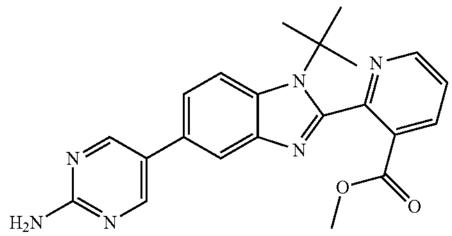 | 2 | 1.2 | 403.4 | A |
| 8 | 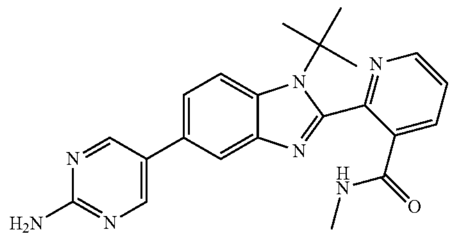 | 3 | 1.1 | 402.4 | A |
| 9 | 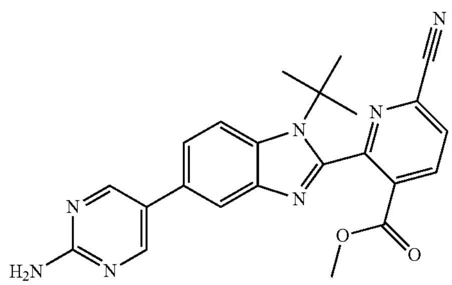 [SMILES: COC(=O)c1ccc(C#N)nc1-c1nc2cc(-c3cnc(N)nc3)ccc2n1C(C)(C)C] | 2 | 1.3 | 428.4 | A |
| 10 | 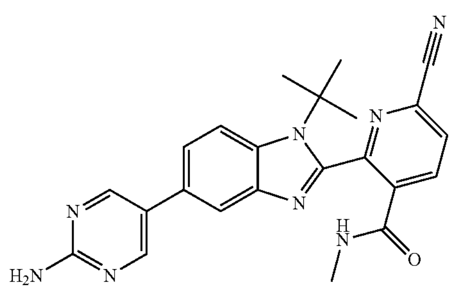 [SMILES: CNC(=O)c1ccc(C#N)nc1-c1nc2cc(-c3cnc(N)nc3)ccc2n1C(C)(C)C] | 3 | 1.2 | 427.4 | A |
| 11 | 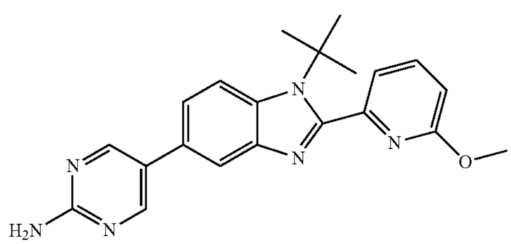 [SMILES: COc1cccc(-c2nc3cc(-c4cnc(N)nc4)ccc3n2C(C)(C)C)n1] | 2 | 6.0 | 375.6 | D |
| 12 | 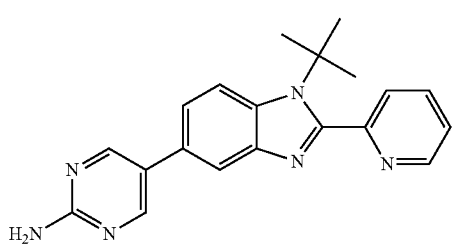 [SMILES: CC(C)(C)n1c(-c2ccccn2)nc2cc(-c3cnc(N)nc3)ccc21] | 2 | 1.0 | 345.2 | A |

TABLE 3-continued
Final Compounds
| Example # | Structure | Method | Retention time (min) | m/z [M + H]+ | LC/MS Method |
|---|---|---|---|---|---|
| 13 | 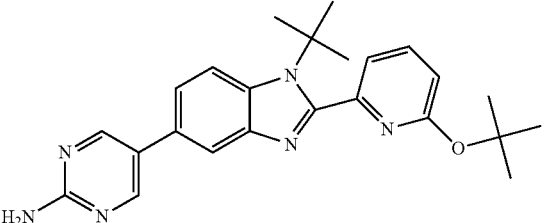 | 2 | 6.7 | 417.7 | D |
| 14 | 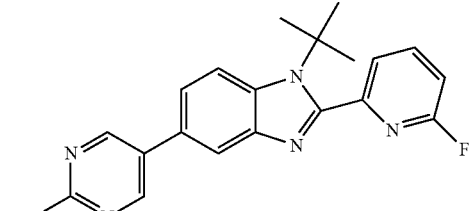 | 2 | 6.1 | 363.6 | D |
| 15 | 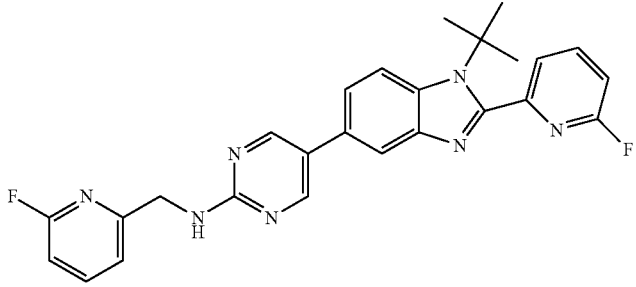 | 2 | 7.0 | 472.6 | D |
| 16 | 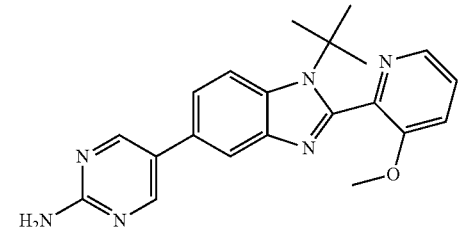 | 2 | 1.1 | 375.2 | B |
| 17 | 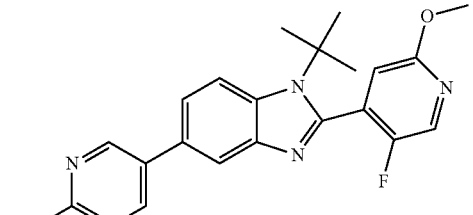 | 2 | 1.3 | 393.2 | A |
| 18 | 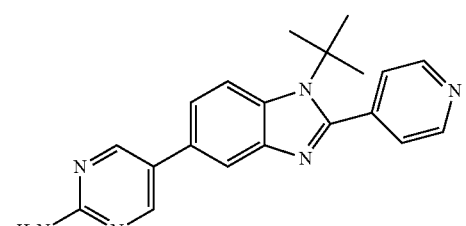 | 2 | 1.3 | 345.5 | C |

TABLE 3-continued

| | Final Compounds | | | | |
|---|---|---|---|---|---|
| Example # | Structure | Method | Retention time (min) | m/z [M + H]⁺ | LC/MS Method |
| 19 | | 2 | 6.3 | 425.5 | D |
| 20 | | 4 | 1.0 | 412.2 | B |
| 21 | | 4 | 1.0 | 430.2 | B |
| 22 | | 4 | 1.1 | 446.2 | B |
| 23 | | 2 | 1.3 | 492.0 | A |

TABLE 3-continued

Final Compounds

| Example # | Structure | Method | Retention time (min) | m/z [M + H]+ | LC/MS Method |
|---|---|---|---|---|---|
| 24 | 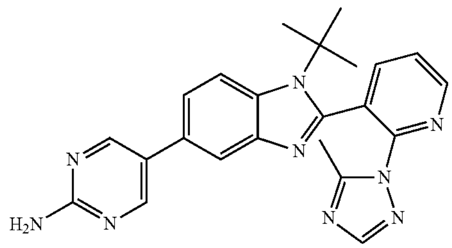 [SMILES: Cc1ncnn1-c1ncccc1-c1nc2cc(-c3cnc(N)nc3)ccc2n1C(C)(C)C] | 4 | 1.2 | 426.2 | A |
| 25 | 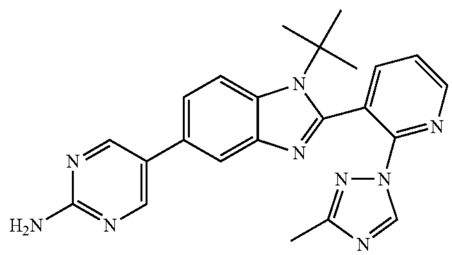 [SMILES: Cc1ncn(-c2ncccc2-c2nc3cc(-c4cnc(N)nc4)ccc3n2C(C)(C)C)n1] | 4 | 1.2 | 426.2 | A |
| 26 | 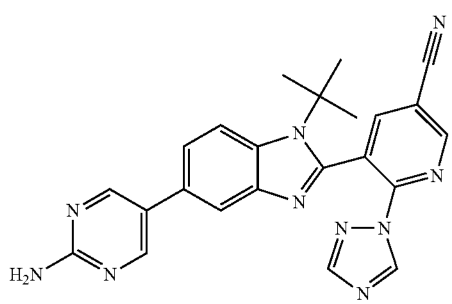 [SMILES: CC(C)(C)n1c(-c2cc(C#N)cnc2-n2cncn2)nc2cc(-c3cnc(N)nc3)ccc21] | 5 | 1.2 | 437.2 | A |
| 27 | 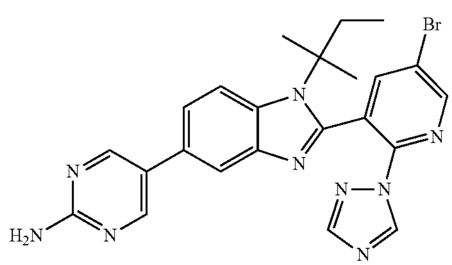 [SMILES: CCC(C)(C)n1c(-c2cc(Br)cnc2-n2cncn2)nc2cc(-c3cnc(N)nc3)ccc21] | 4 | 1.3 | 504.0 | A |
| 28 | 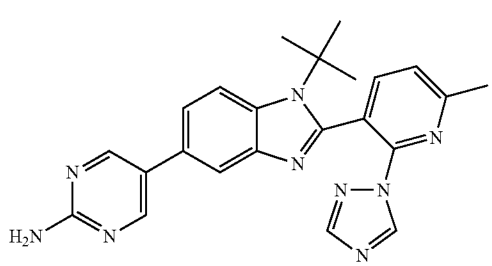 [SMILES: Cc1ccc(-c2nc3cc(-c4cnc(N)nc4)ccc3n2C(C)(C)C)c(-n2cncn2)n1] | 4 | 1.2 | 426.2 | A |

TABLE 3-continued

Final Compounds

| Example # | Structure | Method | Retention time (min) | m/z [M + H]+ | LC/MS Method |
|---|---|---|---|---|---|
| 29 | 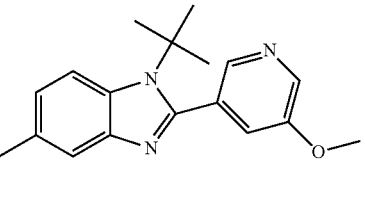 | 2 | 5.6 | 375.6 | D |
| 30 | 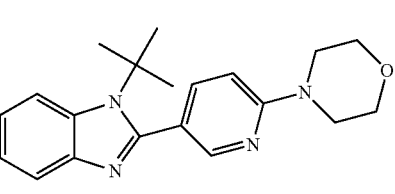 | 2 | 1.0 | 430.2 | A |
| 31 | 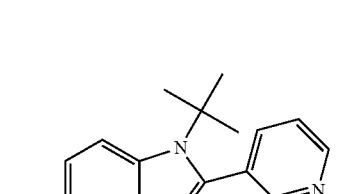 | 2 | 1.0 | 345.2 | A |
| 32 | 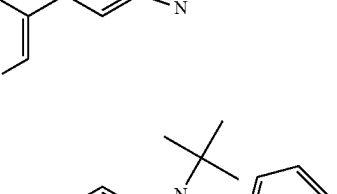 | 2 | 1.1 | 375.2 | B |
| 33 | 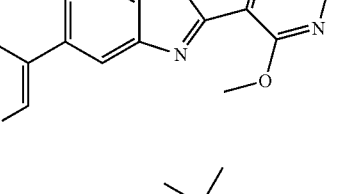 | 2 | 1.2 | 389.2 | B |

Assessment of Biological Properties
1. Binding Assay

Compounds are assessed for the ability to bind to FLAP in a binding assay that measures compound-specific displacement of an iodinated ($^{125}$I) FLAP inhibitor via a Scintillation Proximity Assay format (adapted from S. Charleson et al., Mol. Pharmacol., 1992, 41, 873-879).

Cell pellets produced from sf9 insect cells expressing recombinant human FLAP protein are resuspended in buffer A [15 mM Tris-HCl (pH 7.5), 2 mM MgCl$_2$, 0.3 mM EDTA, 1 mM PMSF]. The cells are lysed with a Dounce homogenizer and the material is centrifuged at 10,000×g for 10 minutes. The supernatant is then collected and centrifuged at 100,000×g for 60 minutes. To prepare membrane protein for an assay, an aliquot of the 100,000×g pellet is resuspended in 1 ml of buffer A, Dounce homogenized, and finally subjected to polytron mixing (30 seconds). Membrane protein (25 µl, 5 µg) is mixed with WGA SPA beads (Amersham) and stirred for 1 h. To an assay plate (Perkin Elmer FlexiPlate) is added 25 µl of test compound prepared in Binding buffer [100 mM Tris (pH 7.5), 140 mM NaCl, 5% glycerol, 2 mM EDTA, 0.5 mM TCEP, 0.05% Tween 20], 25 µl of [$^{125}$I]L-691,831 (an iodinated analog of MK-591, Charleson et al. *Mol. Pharmacol.*, 41, 873-879, 1992) and finally 50 µl of the bead/protein mixture. (final concentrations: beads, 200 μg/well; protein, 5 μg/well; [$^{125}$I] probe, 0 08 nM/well (17 nCi/well). The plates are shaken for 2 h before reading on a Microbeta plate reader. Non-specific binding is determined by the addition of 10 μM cold L-691,831 compound.

In general, the preferred potency range ($IC_{50}$) of compounds in the above assay is between 0.1 nM to 10 μM, the more preferred potency range is 0.1 nM to 1 μM, and the most preferred potency range is 0.1 nM to 100 nM.

2. Whole Blood Assay

Compounds are additionally tested in a human whole blood assay to determine their ability to inhibit the synthesis of $LTB_4$ in a cellular system. Compounds are combined with heparinized human whole blood and incubated for 15 minutes at 37° C. Calcimycin (20 μM final, prepared in phosphate-buffered saline, pH 7.4) is then added and the mixture is incubated for another 30 minutes at 37° C. The samples are centrifuged for 5 min at low speed (1500×g) and the plasma layer is removed. Plasma $LTB_4$ concentrations are then measured using an antibody-based homogenous time-resolved fluorescence method (CisBio, Bedford, Mass.).

In general, the preferred potency range ($IC_{50}$) of compounds in the above assay is between 10 nM to 10 μM, the more preferred potency range is 10 nM to 1 μM.

Method of Use

The compounds of the invention are effective inhibitors of 5-lipoxygenase activating protein (FLAP) and thus inhibit leukotriene production. Therefore, in one embodiment of the invention, there is provided methods of treating leukotriene-mediated disorders using compounds of the invention. In another embodiment, there is provided methods of treating cardiovascular, inflammatory, allergic, pulmonary and fibrotic diseases, renal diseases and cancer using compounds of the invention.

Without wishing to be bound by theory, by inhibiting the activity of FLAP, the compounds of the invention block the production of LTs resulting from the oxidation of arachidonic acid by 5-LO and subsequent metabolism. Thus, the inhibition of FLAP activity is an attractive means for preventing and treating a variety of diseases mediated by LTs. These include:

Cardiovascular diseases including atherosclerosis, myocardial infarction, stroke, aortic aneurysm, sickle cell crisis, ischemia-reperfusion injury, pulmonary arterial hypertension and sepsis;

Allergic diseases including asthma, allergic rhinitis, rhinosinusitis, atopic dermatitis and urticaria;

Fibrotic diseases including airway remodeling in asthma, idiopathic pulmonary fibrosis, scleroderma, asbestosis;

Pulmonary syndromes including adult respiratory distress syndrome, viral bronchiolitis, obstructive sleep apnea, chronic obstructive pulmonary disease, cystic fibrosis, and bronchopulmonary dysplasia;

Inflammatory diseases including rheumatoid arthritis, osteoarthritis, gout, glomerulonephritis, interstitial cystitis, psoriasis, inflammatory bowel disease systemic lupus erythematosus, transplant rejection, multiple sclerosis, inflammatory pain, inflammatory and allergic ocular diseases;

Cancer including solid tumors, leukemias and lymphomas; and

Renal diseases such as glomerulonephritis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems*, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

What is claimed is:

1. A compound of formula IA

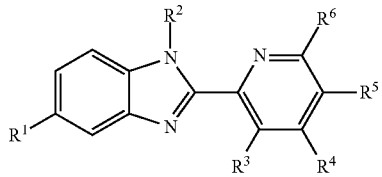

wherein:
$R^1$ is pyridinyl, pyrimidinyl, pyrazinyl, pyridazinyl, pyrrolopyridinyl, imidazopyridinyl, pyrazolopyridinyl or dihydropyrrolopyridinyl optionally substituted with oxo, wherein each heterocycle is optionally independently substituted with one to three groups selected from Ra, Rb and Rc;

$R^2$ is $C_1$-$C_6$ alkyl or $C_{3-6}$ cycloalkyl optionally substituted with $C_{1-3}$ alkyl;

$R^3$ is H, —OH, halogen, —CN, $C_{1-6}$ alkoxy, —COOR$^8$, —C(O)NR$^8$R$^9$ or 5-6 membered heteroaryl ring which is optionally substituted with $C_{1-3}$ alkyl;

$R^4$, $R^5$, and $R^6$ are each independently selected from
  (a) —H,
  (b) —OH,
  (c) halogen,
  (d) —CN,
  (e) —CF$_3$,
  (f) $C_{1-6}$alkyl optionally substituted with one to three —OH, fluorine, $C_{1-6}$alkoxyl —N(R$^8$)(R$^9$), or —C(O)N(R$^8$)(R$^9$),
  (g) $C_{3-6}$cycloalkyl
  (h) $C_{1-6}$alkoxy optionally substituted with one to three —OH, fluorine, —OC$_{1-6}$alkyl, or —OC$_{3-6}$cycloalkyl
  (i) —S(O)$_n$C$_{1-6}$alkyl,
  (j) —S(O)$_2$aryl
  (k) —S(O)$_2$heterocycle
  (l) —CO$_2$R$^8$,
  (m) —SCF$_3$,
  (n') a 5-6 membered heterocyclic ring;

$R^8$ and $R^9$ are each independently selected from —H, $C_{1-6}$alkyl, and 5-6 membered heterocyclic ring;

Ra is selected from H, —NH$_2$, —NH(C$_1$-C$_6$)alkyl, —NR$^{10}$R$^{11}$, —NH—C(O)C$_1$-C$_6$alkyl, NR$^{11}$—C(O)C$_1$-C$_6$alkyl, —O(C$_1$-C$_8$)alkyl, —O(C$_3$-C$_6$)cycloalkyl, —S—(C$_1$-C$_6$)alkyl, —S(O)—C$_1$-C$_6$alkyl, —S(O)$_2$—C$_1$-C$_6$alkyl, and —CH$_2$—OH;

Rb is selected from —H, —(C$_1$-C$_6$)alkyl, —O—(C$_1$-C$_6$)alkyl, —NH$_2$, —CH$_2$—OH, —C≡N, —CH$_2$NH$_2$ and —C(O)OCH$_3$;

Rc is selected from —H, —CH$_3$ and —OH;

$R^{10}$ and $R^{11}$ are each independently selected from —H, $C_{1-6}$alkyl-5-6 membered heterocyclyl, $C_{1-6}$alkyl-5-6 membered heteroaryl optionally substituted with halogen and $C_{1-6}$alkyl-aryl;

n is 0, 1 or 2;

or a pharmaceutically acceptable salt thereof.

2. A compound of formula (IA) according to claim 1, or a pharmaceutically acceptable salt thereof, wherein:
$R^1$ is selected from:

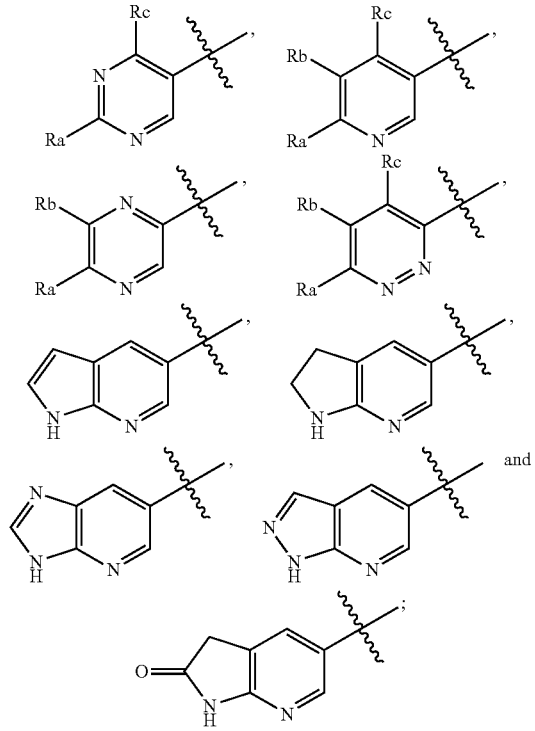

$R^2$ is methyl, ethyl, propyl, isopropyl, butyl, t-butyl, isobutyl, pentyl, hexyl, cyclopropyl, cyclobutyl, cyclopentyl or cyclohexyl, wherein the cycloalkyl group is optionally substituted with a $C_{1-3}$ alkyl group;

$R^3$ is H, —OH, halogen, —CN, $C_{1-6}$ alkoxy, —COOR$^8$, —C(O)NR$^8$R$^9$, pyrrolyl, furanyl, thienyl, imidazolyl, pyrazolyl, triazolyl, pyridinyl, pyrimidinyl, pyrazinyl or pyridazinyl, wherein the heteroaryl ring is optionally substituted with $C_{1-3}$ alkyl;

$R^4$, $R^5$ and $R^6$ are each independently selected from
  (a) —H,
  (b) —OH,
  (c) halogen,
  (d) —CN,
  (e) —CF$_3$,
  (f) $C_{1-6}$alkyl optionally substituted with one to three —OH, fluorine, $C_{1-6}$alkoxyl —N(R$^8$)(R$^9$), or —C(O)N(R$^8$)(R$^9$),
  (g) $C_{3-6}$cycloalkyl
  (h) $C_{1-6}$alkoxy optionally substituted with one to three —OH, fluorine, —OC$_{1-6}$alkyl, or —OC$_{3-6}$cycloalkyl
  (i) —S(O)$_n$C$_{1-6}$alkyl,
  (j) —S(O)$_2$aryl
  (k) —S(O)$_2$heterocycle
  (l) —CO$_2$R$^8$,
  (m) —SCF$_3$,
  (n') a pyrrolidinyl, tetrahydrofuranyl, tetrahydrothienyl, piperidinyl, morpholinyl, thiomorpholinyl, dioxothiomorpholinyl and tetrahydropyranyl;

$R^8$ and $R^9$ are each independently selected from —H, $C_{1-6}$alkyl, pyrrolidinyl, tetrahydrofuranyl, tetrahydrothienyl, piperidinyl, morpholinyl, thiomorpholinyl, dioxothiomorpholinyl and tetrahydropyranyl;

Ra is selected from H, —NH$_2$, —NH(C$_1$-C$_6$)alkyl, —NR$^{10}$R$^{11}$, —NH—C(O)C$_1$-C$_6$alkyl, NR$^{11}$—C(O)C$_1$-C$_6$alkyl, —O(C$_1$-C$_8$)alkyl, —O(C$_3$-C$_6$)cycloalkyl, —S—(C$_1$-C$_6$)alkyl, —S(O)—C$_1$-C$_6$alkyl, —S(O)$_2$—C$_1$-C$_6$alkyl and —CH$_2$—OH;

Rb is selected from —H, —(C$_1$-C$_6$)alkyl, —O—(C$_1$-C$_6$)alkyl, —NH$_2$, —CH$_2$—OH, —C≡N, —CH$_2$NH$_2$ and —C(O)OCH$_3$;

Rc is selected from —H, —CH$_3$ and, —OH;

R$^{10}$ and R$^{11}$ are each independently selected from —H, C$_{1-6}$alkyl, C$_{1-6}$alkyl-5-6 membered heterocyclyl, C$_{1-6}$alkyl-5-6 membered heteroaryl optionally substituted with fluoro and C$_{1-6}$alkyl-phenyl;

n is 0, 1 or 2.

3. A compound of formula (IA) according to claim 1, wherein:

R$^1$ is selected from:

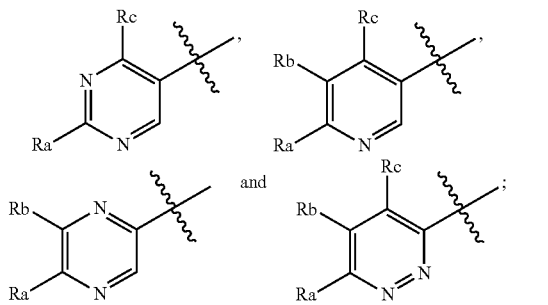

Ra is selected from H, —NH$_2$, —NH(C$_1$-C$_6$)alkyl, —NR$^{10}$R$^{11}$, —NH—C(O)C$_1$-C$_6$alkyl, NR$^{11}$—C(O)C$_1$-C$_6$alkyl, —O(C$_1$-C$_8$)alkyl, —O(C$_3$-C$_6$)cycloalkyl, —S—(C$_1$-C$_6$)alkyl, —S(O)—C$_1$-C$_6$alkyl, —S(O)$_2$—C$_1$-C$_6$alkyl and —CH$_2$—OH;

Rb is selected from —H, —(C$_1$-C$_6$)alkyl, —O—(C$_1$-C$_6$)alkyl, —NH$_2$, —CH$_2$—OH, —C≡N, —CH$_2$NH$_2$ and —C(O)OCH$_3$;

Rc is selected from —H, —CH$_3$ and, —OH;

R$^{10}$ and R$^{11}$ are each independently selected from —H, C$_{1-6}$alkyl, C$_{1-6}$alkyl-5-6 membered heterocyclyl, C$_{1-6}$alkyl-fluorpyridine and C$_{1-6}$alkyl-phenyl;

or a pharmaceutically acceptable salt thereof.

4. A compound of formula (IA) according to claim 1, wherein:

R$^2$ is methyl, ethyl, propyl, isopropyl, butyl, t-butyl, isobutyl, cyclopropyl, cyclobutyl or cyclopentyl, wherein the cycloalkyl group is optionally substituted with methyl;

or a pharmaceutically acceptable salt thereof.

5. A compound of formula (IA) according to claim 1, wherein:

R$^3$ is H, —OH, halogen, —CN, C$_{1-6}$ alkoxy, —COOR$^8$, —C(O)NR$^8$R$^9$, pyrrolyl, furanyl, thienyl, imidazolyl, pyrazolyl, triazolyl, pyridinyl, pyrimidinyl, pyrazinyl or pyridazinyl, wherein the heteroaryl ring is optionally substituted with C$_{1-3}$ alkyl;

R$^4$, R$^5$ and R$^6$ are each independently selected from
(a) —H,
(b) —OH,
(c) halogen,
(d) —CN,
(e) —CF$_3$,
(f) C$_{1-6}$alkyl optionally substituted with one to three —OH, fluorine, C$_{1-6}$alkoxyl —N(R$^8$)(R$^9$), or —C(O)N(R$^8$)(R$^9$),
(g) C$_{3-6}$cycloalkyl
(h) C$_{1-6}$alkoxy optionally substituted with one to three —OH, fluorine, —OC$_{1-6}$alkyl, or —OC$_{3-6}$cycloalkyl
(i) —S(O)$_2$C$_{1-6}$alkyl,
(j) —S(O)$_2$aryl
(k) —S(O)$_2$heterocycle
(l) —CO$_2$R$^8$,
(m) —SCF$_3$,
(n') a pyrrolidinyl, tetrahydrofuranyl, tetrahydrothienyl, piperidinyl, morpholinyl, thiomorpholinyl, dioxothiomorpholinyl and tetrahydropyranyl;

R$^8$ and R$^9$ are each independently selected from —H, C$_{1-6}$alkyl, pyrrolidinyl, tetrahydrofuranyl, tetrahydrothienyl, piperidinyl, morpholinyl, thiomorpholinyl, dioxothiomorpholinyl and tetrahydropyranyl;

or a pharmaceutically acceptable salt thereof.

6. A compound of formula (IA) according to claim 1, wherein:

R$^1$ is selected from:

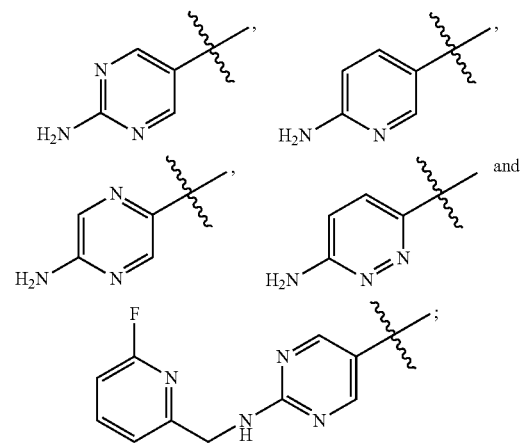

R$^2$ is t-butyl or cyclobutyl optionally substituted with a methyl group;

R$^3$ is —H, C$_{1-3}$ alkoxy, —COOR$^8$, —C(O)NR$^8$R$^9$ or triazolyl which is optionally substituted with a methyl group;

R$^4$, R$^5$ and R$^6$ are each independently selected from
(a) —H,
(b) —OH,
(c) halogen,
(d) —CN,
(e) —CF$_3$,
(f) C$_{1-6}$alkyl optionally substituted with one to three —OH, fluorine, C$_{1-6}$alkoxyl —N(R$^8$)(R$^9$), or —C(O)N(R$^8$)(R$^9$),
(g) C$_{3-6}$cycloalkyl
(h) C$_{1-6}$alkoxy optionally substituted with one to three —OH, fluorine, —OC$_{1-6}$alkyl, or —OC$_{3-6}$cycloalkyl;

R$^8$ and R$^9$ are each independently selected from —H and C$_{1-6}$alkyl;

or a pharmaceutically acceptable salt thereof.

7. A compound of formula (IA) according to claim 6, or a pharmaceutically acceptable salt thereof, wherein:
R¹ is

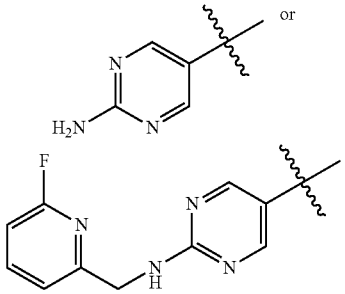

8. A compound of formula (IA) according to claim 6, wherein:
R² is t-butyl or cyclobutyl optionally substituted with a methyl group;
or a pharmaceutically acceptable salt thereof.

9. A compound of formula (IA) according to claim 6, wherein:
R¹ is

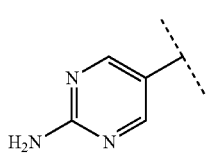

R² is t-butyl;
R³ is selected from

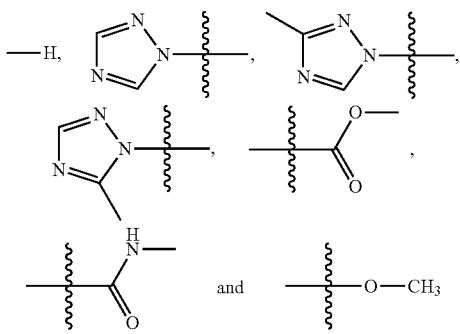

R⁴, R⁵ and R⁶ are each independently selected from —H, —CN, F, cyclopropyl, methoxy and t-butoxy;
or a pharmaceutically acceptable salt thereof.

10. A compound of formula (IA) according to claim 9, wherein:
R² is

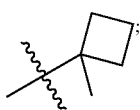 [SMILES: *C1(C)CCC1]

or a pharmaceutically acceptable salt thereof.

11. A compound of formula IB

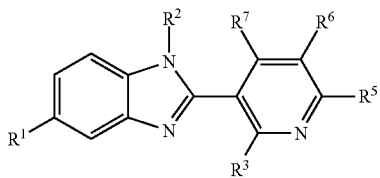

wherein:
R¹ is pyridinyl, pyrimidinyl, pyrazinyl, pyridazinyl, pyrrolopyridinyl, imidazopyridinyl, pyrazolopyridinyl or dihydropyrrolopyridinyl optionally substituted with oxo, wherein each heterocycle is optionally independently substituted with one to three groups selected from Ra, Rb and Rc;

R² is $C_1$-$C_6$ alkyl or $C_{3-6}$ cycloalkyl optionally substituted with $C_{1-3}$ alkyl;

R³ is H, —OH, halogen, —CN, $C_{1-6}$ alkoxy, —COOR⁸, —C(O)NR⁸R⁹ or 5-6 membered heteroaryl ring which is optionally substituted with $C_{1-3}$ alkyl;

R⁵, R⁶, and R⁷ are each independently selected from
(a) —H,
(b) —OH,
(c) halogen,
(d) —CN,
(e) —CF₃,
(f) $C_{1-6}$alkyl optionally substituted with one to three —OH, fluorine, $C_{1-6}$alkoxyl —N(R⁸)(R⁹), or —C(O)N(R⁸)(R⁹),
(g) $C_{3-6}$cycloalkyl
(h) $C_{1-6}$alkoxy optionally substituted with one to three —OH, fluorine, —O$C_{1-6}$alkyl, or —O$C_{3-6}$cycloalkyl
(i) —S(O)$_n$$C_{1-6}$alkyl,
(j) —S(O)₂aryl
(k) —S(O)₂ heterocycle
(l) —CO₂R⁸,
(m) —SCF₃,
(n') a 5-6 membered heterocyclic ring;

R⁸ and R⁹ are each independently selected from —H, $C_{1-6}$alkyl, and 5-6 membered heterocyclic ring;

Ra is selected from H, —NH₂, —NH($C_1$-$C_6$)alkyl, —NR¹⁰R¹¹, —NH—C(O)$C_1$-$C_6$alkyl, NR¹¹—C(O)$C_1$-$C_6$alkyl, —O($C_1$-$C_8$)alkyl, —O($C_3$-$C_6$)cycloalkyl, —S—($C_1$-$C_6$)alkyl, —S(O)—$C_1$-$C_6$alkyl, —S(O)₂—$C_1$-$C_6$alkyl, and —CH₂—OH;

Rb is selected from —H, —($C_1$-$C_6$)alkyl, —O—($C_1$-$C_6$)alkyl, —NH₂, —CH₂—OH, —C≡N, —CH₂NH₂ and —C(O)OCH₃;

Rc is selected from —H, —CH₃ and, —OH;

R¹⁰ and R¹¹ are each independently selected from —H, $C_{1-6}$alkyl, $C_{1-6}$alkyl-5-6 membered heterocyclyl, $C_{1-6}$alkyl-5-6 membered heteroaryl optionally substituted with halogen and $C_{1-6}$alkyl-aryl;

n is 0, 1 or 2;

or a pharmaceutically acceptable salt thereof.

12. A compound of formula (IB) according to claim 11, or a pharmaceutically acceptable salt thereof, wherein:

$R^1$ is selected from:

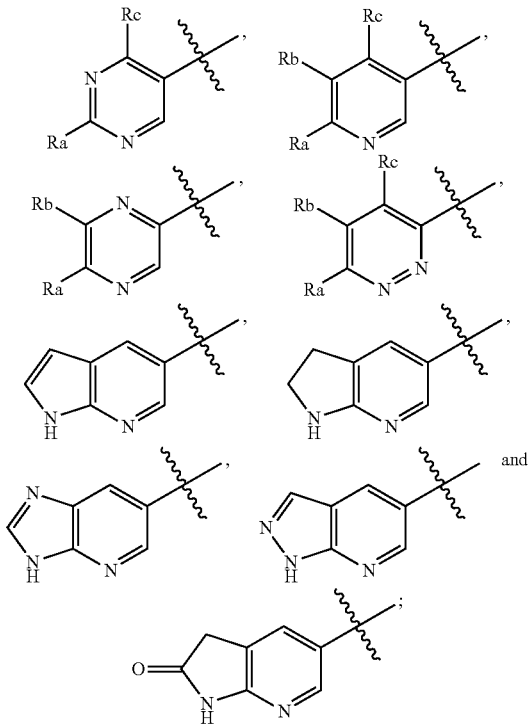

$R^2$ is methyl, ethyl, propyl, isopropyl, dimethylpropyl, butyl, t-butyl, isobutyl, pentyl, hexyl, cyclopropyl, cyclobutyl, cyclopentyl or cyclohexyl, wherein the cycloalkyl group is optionally substituted with a $C_{1-3}$ alkyl group;

$R^3$ is H, —OH, halogen, —CN, $C_{1-6}$ alkoxy, —COOR$^8$, —C(O)NR$^8$R$^9$, pyrrolyl, furanyl, thienyl, imidazolyl, pyrazolyl, triazolyl, pyridinyl, pyrimidinyl, pyrazinyl or pyridazinyl, wherein the heteroaryl ring is optionally substituted with $C_{1-3}$ alkyl;

$R^5$, $R^6$ and $R^7$ are each independently selected from
(a) —H,
(b) —OH,
(c) halogen,
(d) —CN,
(e) —CF$_3$,
(f) $C_{1-6}$alkyl optionally substituted with one to three —OH, fluorine, $C_{1-6}$alkoxyl —N(R$^8$)(R$^9$), or —C(O)N(R$^8$)(R$^9$),
(g) $C_{3-6}$cycloalkyl
(h) $C_{1-6}$alkoxy optionally substituted with one to three —OH, fluorine, —OC$_{1-6}$alkyl, or —OC$_{3-6}$cycloalkyl
(i) —S(O)$_n$C$_{1-6}$alkyl,
(j) —S(O)$_2$aryl
(k) —S(O)$_2$ heterocycle
(l) —CO$_2$R$^8$,
(m) —SCF$_3$,
(n') a pyrrolidinyl, tetrahydrofuranyl, tetrahydrothienyl, piperidinyl, morpholinyl, thiomorpholinyl, dioxothiomorpholinyl and tetrahydropyranyl;

$R^8$ and $R^9$ are each independently selected from —H, $C_{1-6}$alkyl, pyrrolidinyl, tetrahydrofuranyl, tetrahydrothienyl, piperidinyl, morpholinyl, thiomorpholinyl, dioxothiomorpholinyl and tetrahydropyranyl;

Ra is selected from H, —NH$_2$, —NH(C$_1$-C$_6$)alkyl, —NR$^{10}$R$^{11}$, —NH—C(O)C$_1$-C$_6$alkyl, NR$^{11}$—C(O)C$_1$—C$_6$alkyl, —O(C$_1$-C$_8$)alkyl, —O(C$_3$-C$_6$)cycloalkyl, —S—(C$_1$-C$_6$)alkyl, —S(O)—C$_1$-C$_6$alkyl, —S(O)$_2$—C$_1$-C$_6$alkyl, and —CH$_2$—OH;

Rb is selected from —H, —(C$_1$-C$_6$)alkyl, —O—(C$_1$-C$_6$)alkyl, —NH$_2$, —CH$_2$—OH, —C≡N, —CH$_2$NH$_2$ and —C(O)OCH$_3$;

Rc is selected from —H, —CH$_3$ and, —OH;

$R^{10}$ and $R^{11}$ are each independently selected from —H, $C_{1-6}$alkyl, $C_{1-6}$alkyl-5-6 membered heterocyclyl, $C_{1-6}$alkyl-fluoropyridine and $C_{1-6}$alkyl-phenyl];

n is 0, 1 or 2.

13. A compound of formula (IB) according to claim 11, wherein:

$R^1$ is selected from:

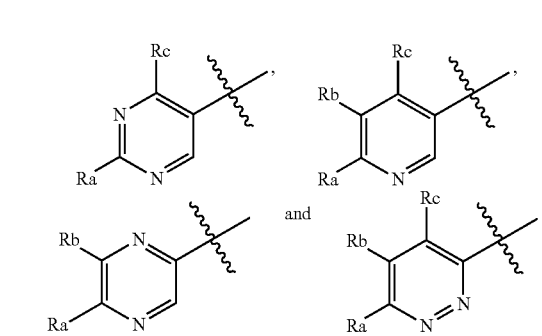

Ra is selected from H, —NH$_2$, —NH(C$_1$-C$_6$)alkyl, —NR$^{10}$R$^{11}$, —NH—C(O)C$_1$-C$_6$alkyl, NR$^{11}$—C(O)C$_1$-C$_6$alkyl, —O(C-C$_8$)alkyl, —O(C$_3$-C$_6$)cycloalkyl, —S—(C$_1$-C$_6$)alkyl, —S(O)—C$_1$-C$_6$alkyl, —S(O)$_2$—C$_1$-C$_6$alkyl and —CH$_2$—OH;

Rb is selected from —H, —(C$_1$-C$_6$)alkyl, —O—(C$_1$-C$_6$)alkyl, —NH$_2$, —CH$_2$—OH, —C≡N, —CH$_2$NH$_2$ and —C(O)OCH$_3$;

Rc is selected from —H, —CH$_3$ and, —OH;

$R^{10}$ and $R^{11}$ are each independently selected from —H, $C_{1-6}$alkyl, $C_{1-6}$alkyl—5-6 membered heterocyclyl, $C_{1-6}$alkyl-fluoropyridine and $C_{1-6}$alkyl-phenyl;

or a pharmaceutically acceptable salt thereof.

14. A compound of formula (IB) according to claim 11, wherein:

$R^2$ is methyl, ethyl, propyl, isopropyl, dimethylpropyl, butyl, t-butyl or isobutyl;

or a pharmaceutically acceptable salt thereof.

15. A compound of formula (IB) according to claim 11, wherein:

$R^3$ is H, —OH, halogen, —CN, $C_{1-6}$ alkoxy, —COOR$^8$, —C(O)NR$^8$R$^9$, pyrrolyl, furanyl, thienyl, imidazolyl, pyrazolyl, triazolyl, pyridinyl, pyrimidinyl, pyrazinyl or pyridazinyl, wherein the heteroaryl ring is optionally substituted with $C_{1-3}$ alkyl;

$R^5$, $R^6$ and $R^7$ are each independently selected from
(a) —H,
(b) —OH,
(c) halogen,
(d) —CN,
(e) —CF$_3$,
(f) $C_{1-6}$alkyl optionally substituted with one to three —OH, fluorine, $C_{1-6}$alkoxyl —N(R$^8$)(R$^9$), or —C(O)N(R$^8$)(R$^9$), (g) $C_{3-6}$ cycloalkyl
(h) $C_{1-6}$alkoxy optionally substituted with one to three —OH, fluorine, —$OC_{1-6}$alkyl, or —$OC_{3-6}$cycloalkyl
(i) —$S(O)_2C_{1-6}$alkyl,
(j) —$S(O)_2$aryl
(k) —$S(O)_2$ heterocycle
(l) —$CO_2R^8$,
(m) —$SCF_3$,
(n') a pyrrolidinyl, tetrahydrofuranyl, tetrahydrothienyl, piperidinyl, morpholinyl, thiomorpholinyl, dioxothiomorpholinyl and tetrahydropyranyl;

$R^8$ and $R^9$ are each independently selected from —H, $C_{1-6}$alkyl, pyrrolidinyl, tetrahydrofuranyl, tetrahydrothienyl, piperidinyl, morpholinyl, thiomorpholinyl, dioxothiomorpholinyl and tetrahydropyranyl;

or a pharmaceutically acceptable salt thereof.

16. A compound of formula (IB) according to claim 11, wherein:
$R^1$ is selected from:

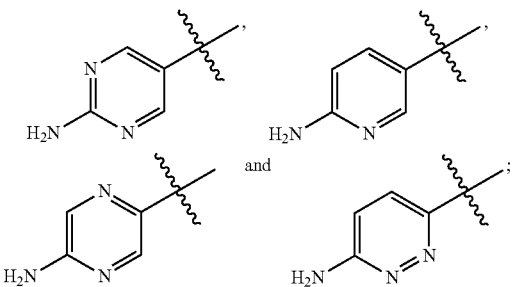

$R^2$ is t-butyl or dimethylpropyl;
$R^3$ is —H, $C_{1-3}$ alkoxy, or triazolyl which is optionally substituted with a methyl group;
$R^5$, $R^6$ and $R^7$ are each independently selected from
(a) —H,
(b) —OH,
(c) halogen,
(d) —CN,
(e) —$CF_3$,
(f) $C_{1-6}$alkyl optionally substituted with one to three —OH, fluorine, $C_{1-6}$alkoxyl —$N(R^8)(R^9)$, or —$C(O)N(R^8)(R^9)$,
(g) $C_{3-6}$cycloalkyl,
(h) $C_{1-6}$alkoxy optionally substituted with one to three —OH, fluorine, —$OC_{1-6}$alkyl, or —$OC_{3-6}$ cycloalkyl,
(i) morpholinyl or piperidinyl;
$R^8$ and $R^9$ are each independently selected from —H and $C_{1-6}$alkyl;
or a pharmaceutically acceptable salt thereof.

17. A compound of formula (IB) as described in claim 16, or a pharmaceutically acceptable salt thereof, wherein:
$R^1$ is

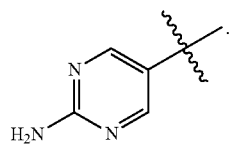

18. A compound of formula (IB) as described in claim 16, wherein:

$R^2$ is t-butyl or dimethylpropyl;
or a pharmaceutically acceptable salt thereof.

19. A compound of formula (IB) according to claim 16, wherein:
$R^1$ is

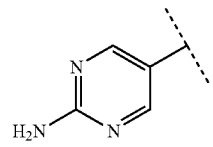

$R^2$ is t-butyl or dimethylpropyl;
$R^3$ is selected from

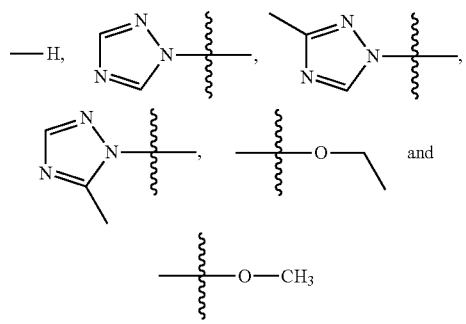

$R^5$, $R^6$ and $R^7$ are each independently selected from —H, —CN, F, Cl, Br, methyl, morpholinyl and methoxy;
or a pharmaceutically acceptable salt thereof.

20. A compound of formula (IB) according to claim 19, wherein:
$R^2$ is t-butyl;
$R^3$ is selected from

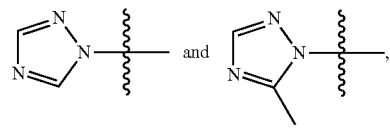

$R^5$, $R^6$ and $R^7$ are each independently selected from —H, methyl and Br;
or a pharmaceutically acceptable salt thereof.

21. A compound of formula IC

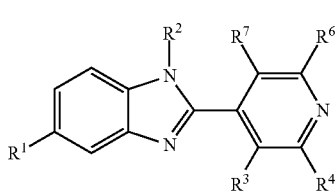

wherein:
$R^1$ is pyridinyl, pyrimidinyl, pyrazinyl, pyridazinyl, pyrrolopyridinyl, imidazopyridinyl, pyrazolopyridinyl or dihydropyrrolopyridinyl optionally substituted with oxo, wherein each heterocycle is optionally independently substituted with one to three groups selected from Ra, Rb and Rc;

R² is C₁-C₆ alkyl or C₃₋₆ cycloalkyl optionally substituted with C₁₋₃ alkyl;

R³ is H, —OH, halogen, —CN, C₁₋₆ alkoxy, —COOR⁸, —C(O)NR⁸R⁹ or 5-6 membered heteroaryl ring which is optionally substituted with C₁₋₃ alkyl;

R⁴, R⁶, and R⁷ are each independently selected from
(a) —H,
(b) —OH,
(c) halogen,
(d) —CN,
(e) —CF₃,
(f) C₁₋₆alkyl optionally substituted with one to three —OH, fluorine, C₁₋₆alkoxyl —N(R⁸)(R⁹), or —C(O)N(R⁸)(R⁹),
(g) C₃₋₆ cycloalkyl
(h) C₁₋₆alkoxy optionally substituted with one to three —OH, fluorine, —OC₁₋₆alkyl, or —OC₃₋₆ cycloalkyl
(i) —S(O)ₙC₁₋₆alkyl,
(j) —S(O)₂aryl
(k) —S(O)₂ heterocycle
(l) —CO₂R⁸,
(m) —SCF₃,
(n') a 5-6 membered heterocyclic ring;

R⁸ and R⁹ are each independently selected from —H, C₁₋₆alkyl, and 5-6 membered heterocyclic ring;

Ra is selected from H, —NH₂, —NH(C₁-C₆)alkyl, —NR¹⁰R¹¹, —NH—C(O)C₁-C₆alkyl, NR¹¹—C(O)C₁-C₆alkyl, —O(C₁-C₈)alkyl, —O(C₃-C₆)cycloalkyl, —S—(C₁-C₆)alkyl, 13 S(O)—C₁-C₆alkyl, —S(O)₂—C₁-C₆alkyl, and —CH₂—OH;

Rb is selected from —H, —(C₁-C₆)alkyl, —O—(C₁-C₆)alkyl, —NH₂, —CH₂—OH, —C≡N, —CH₂NH₂ and —C(O)OCH₃;

Rc is selected from —H, —CH₃ and, —OH;

R¹⁰ and R¹¹ are each independently selected from —H, C₁₋₆alkyl, C₁₋₆alkyl-5-6 membered heterocyclyl, C₁₋₆alkyl-5-6 membered heteroaryl optionally substituted with halogen and C₁₋₆alkyl-aryl;

n is 0, 1 or 2;

or a pharmaceutically acceptable salt thereof.

22. A compound of formula (IC) according to claim 21, or a pharmaceutically acceptable salt thereof, wherein:

R¹ is selected from:

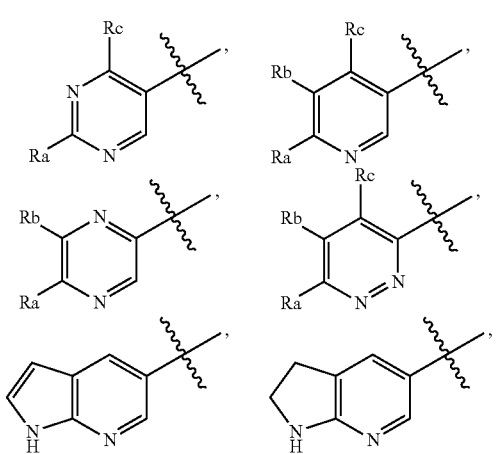

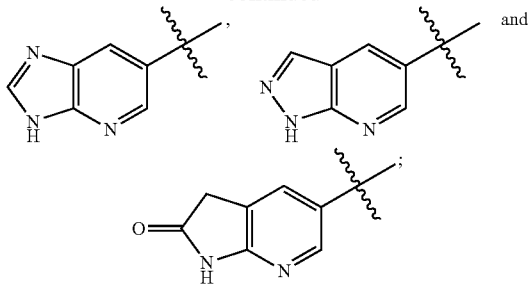

R² is methyl, ethyl, propyl, isopropyl, dimethylpropyl, butyl, t-butyl, isobutyl, pentyl, hexyl, cyclopropyl, cyclobutyl, cyclopentyl or cyclohexyl, wherein the cycloalkyl group is optionally substituted with a C₁₋₃ alkyl group;

R³ is H, —OH, halogen, —CN, C₁₋₆ alkoxy, —COOR⁸, —C(O)NR⁸R⁹, pyrrolyl, furanyl, thienyl, imidazolyl, pyrazolyl, triazolyl, pyridinyl, pyrimidinyl, pyrazinyl or pyridazinyl, wherein the heteroaryl ring is optionally substituted with C₁₋₃ alkyl;

R⁴, R⁶ and R⁷ are each independently selected from
(a) —H,
(b) —OH,
(c) halogen,
(d) —CN,
(e) —CF₃,
(f) C₁₋₆alkyl optionally substituted with one to three —OH, fluorine, C₁₋₆alkoxyl —N(R⁸)(R⁹), or —C(O)N(R⁸)(R⁹),
(g) C₃₋₆ cycloalkyl
(h) C₁₋₆alkoxy optionally substituted with one to three —OH, fluorine, —OC₁₋₆alkyl, or —OC₃₋₆ cycloalkyl
(i) —S(O)ₙC₁₋₆alkyl,
(j) —S(O)₂aryl
(k) —S(O)₂heterocycle
(l) —CO₂R⁸,
(m) —SCF₃,
(n') a pyrrolidinyl, tetrahydrofuranyl, tetrahydrothienyl, piperidinyl, morpholinyl, thiomorpholinyl, dioxothiomorpholinyl and tetrahydropyranyl;

R⁸ and R⁹ are each independently selected from —H, C₁₋₆alkyl, pyrrolidinyl, tetrahydrofuranyl, tetrahydrothienyl, piperidinyl, morpholinyl, thiomorpholinyl, dioxothiomorpholinyl and tetrahydropyranyl;

Ra is selected from H, —NH₂, —NH(C₁₋₆)alkyl, —NR¹⁰R¹¹, —NH—C(O)C₁-C₆alkyl, NR¹¹—C(O)C₁-C₆alkyl, —O(C₁-C₈)alkyl, —O(C₃-C₆)cycloalkyl, —S—(C₁-C₆)alkyl, —S(O)—C₁-C₆alkyl, —S(O)₂—C₁-C₆alkyl, oxo and —CH₂—OH;

Rb is selected from —H, —(C₁-C₆)alkyl, —O—(C₁-C₆)alkyl, —NH₂, —CH₂—OH, —C≡N, —CH₂NH₂ and —C(O)OCH₃;

Rc is selected from —H, —CH₃ and, —OH;

R¹⁰ and R¹¹ are each independently selected from —H, C₁₋₆alkyl, C₁₋₆alkyl-5-6 membered heterocyclyl, C₁₋₆alkyl-fluoropyridine and C₁₋₆alkyl-phenyl;

n is 0,1 or 2.

23. A compound of formula (IC) as described in claim 21, wherein:

R$^1$ is selected from:

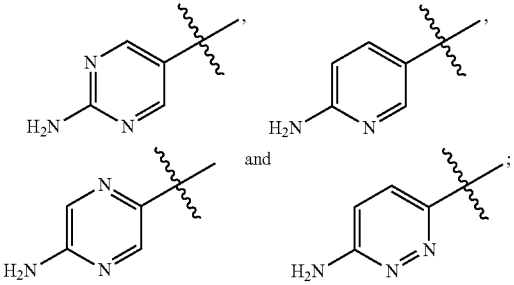

or a pharmaceutically acceptable salt thereof.

24. A compound of formula (IC) as described in claim 21, wherein:

R$^2$ is methyl, ethyl, propyl, isopropyl, dimethylpropyl, butyl, t-butyl or isobutyl;

or a pharmaceutically acceptable salt thereof.

25. A compound of formula (IC) as described in claim 21, wherein:

R$^3$ is H, —OH, halogen, —CN, C$_{1-6}$ alkoxy, —COOR$^8$, —C(O)NR$^8$R$^9$, pyrrolyl, furanyl, thienyl, imidazolyl, pyrazolyl, triazolyl, pyridinyl, pyrimidinyl, pyrazinyl or pyridazinyl, wherein the heteroaryl ring is optionally substituted with C$_{1-3}$ alkyl;

R$^4$, R$^6$ and R$^7$ are each independently selected from
  (a) —H,
  (b) —OH,
  (c) halogen,
  (d) —CN,
  (e) —CF$_3$,
  (f) C$_{1-6}$alkyl optionally substituted with one to three —OH, fluorine, C$_{1-6}$alkoxyl —N(R$^8$)(R$^9$), or —C(O)N(R$^8$)(R$^9$),
  (g) C$_{3-6}$cycloalkyl
  (h) C$_{1-6}$alkoxy optionally substituted with one to three —OH, fluorine, —OC$_{1-6}$alkyl, or —OC$_{3-6}$ cycloalkyl
  (i) —S(O)$_2$C$_{1-6}$alkyl,
  (j) —S(O)$_2$aryl
  (k) —S(O)$_2$ heterocycle
  (l) —CO$_2$R$^8$,
  (m) —SCF$_3$,
  (n') a pyrrolidinyl, tetrahydrofuranyl, tetrahydrothienyl, piperidinyl, morpholinyl, thiomorpholinyl, dioxothiomorpholinyl and tetrahydropyranyl;

R$^8$ and R$^9$ are each independently selected from —H, C$_{1-6}$alkyl, pyrrolidinyl, tetrahydrofuranyl, tetrahydrothienyl, piperidinyl, morpholinyl, thiomorpholinyl, dioxothiomorpholinyl and tetrahydropyranyl;

or a pharmaceutically acceptable salt thereof.

26. A compound of formula (IC) as described in claim 21, wherein:

R$^1$ is selected from:

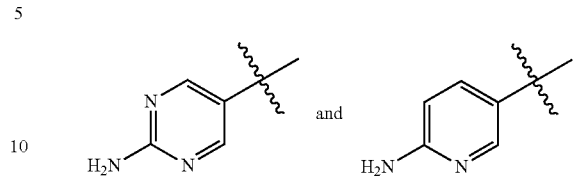

R$^2$ is t-butyl;
R$^3$ is —H or halogen;
R$^4$, R$^6$ and R$^7$ are each independently selected from
  (a) —H,
  (b) —OH,
  (c) halogen,
  (d) —CN,
  (e) —CF$_3$,
  (f) C$_{1-6}$alkyl;
  (g) C$_{3-6}$ cycloalkyl,
  (h) C$_{1-6}$alkoxy optionally substituted with one to three —OH, fluorine, —OC$_{1-6}$alkyl, or —OC$_{3-6}$ cycloalkyl;

or a pharmaceutically acceptable salt thereof.

27. A compound of formula (IC) as described in claim 26, or a pharmaceutically acceptable salt thereof,
wherein R$^1$ is

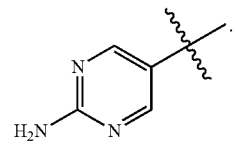

28. A compound of formula (IC) as described in claim 26, wherein:
R$^2$ is t-butyl;
or a pharmaceutically acceptable salt thereof.

29. A compound of formula (IC) according to claim 26, wherein:
R$^1$ is

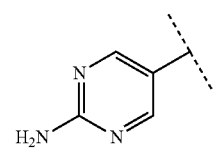

R$^2$ is t-butyl;
R$^3$ is F;
R$^4$, R$^6$ and R$^7$ are each independently selected from —H, Br and methoxy;
or a pharmaceutically acceptable salt thereof.

30. A compound selected from a group consisting of:
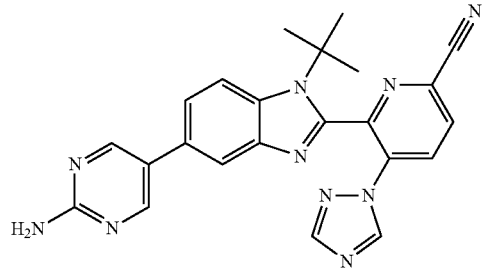
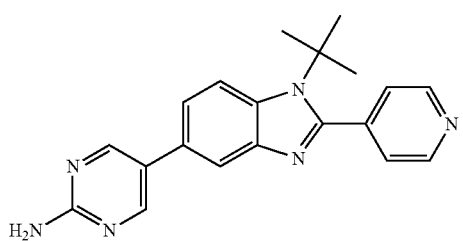
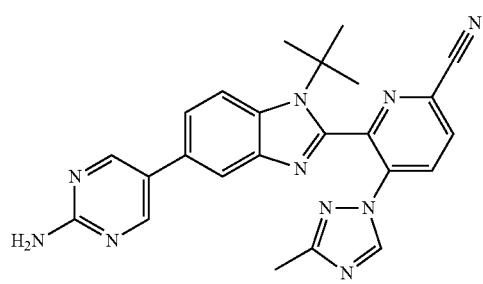
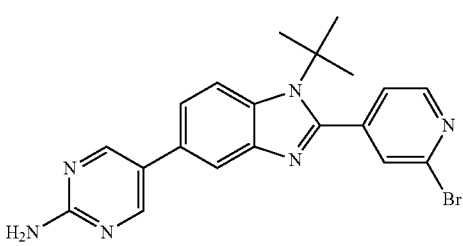
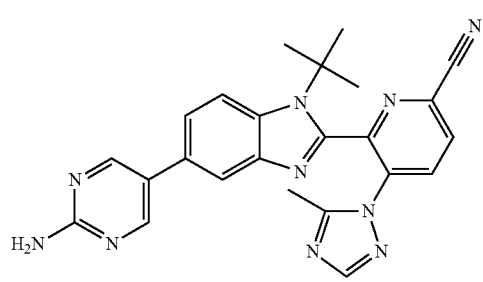
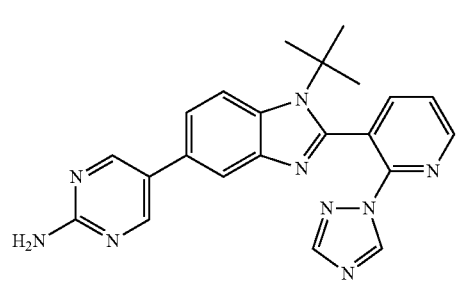 [SMILES: CC(C)(C)n1c(-c2cccnc2-n2cncn2)nc2cc(-c3cnc(N)nc3)ccc21]
-continued
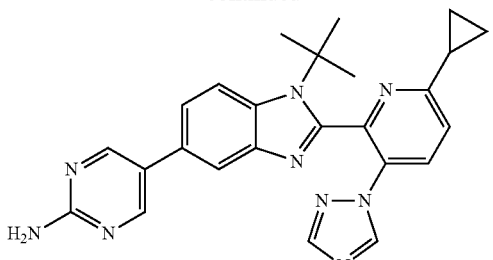
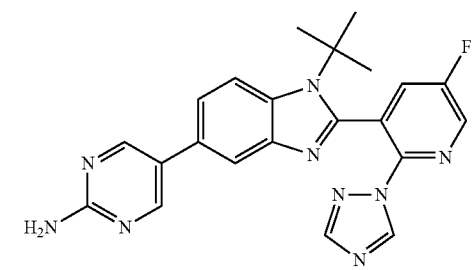
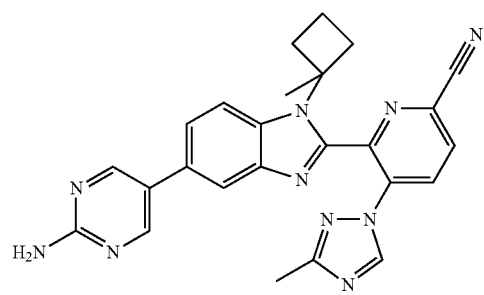
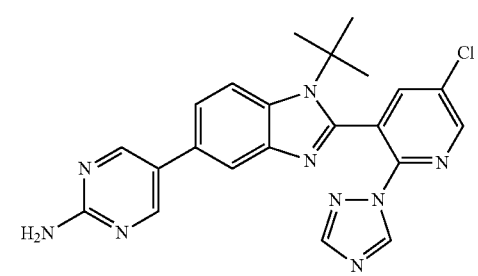
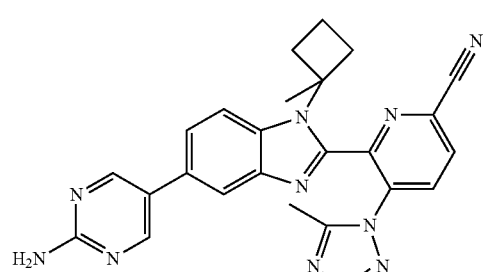
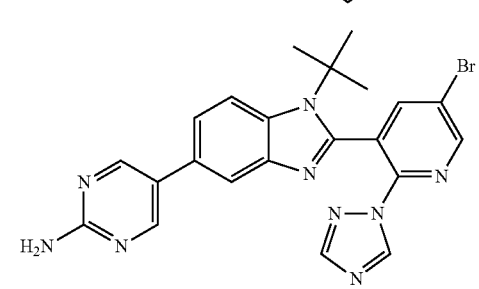

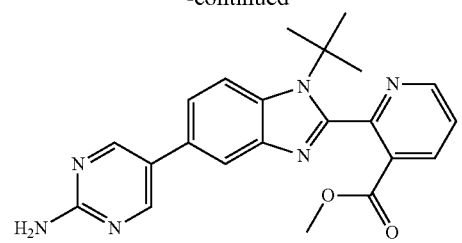
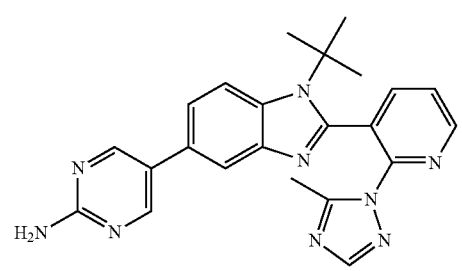
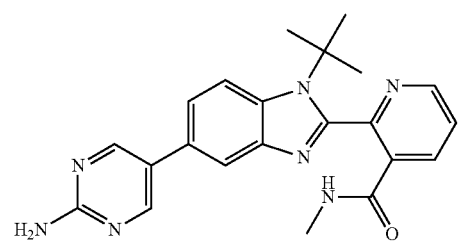
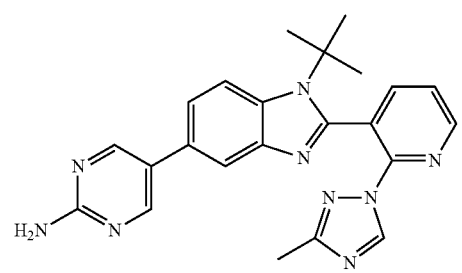
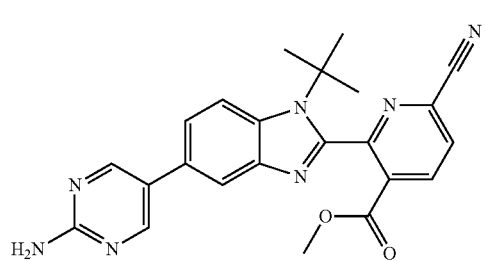
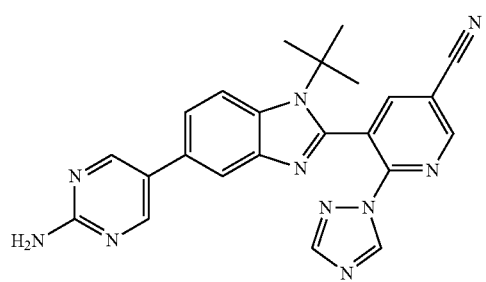
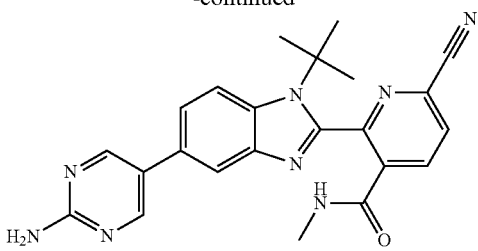
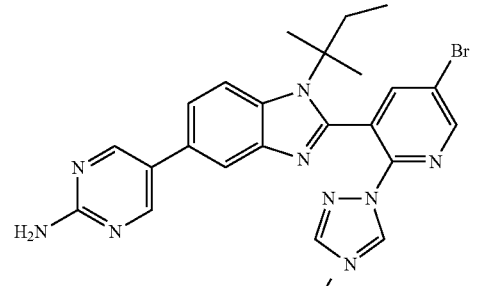
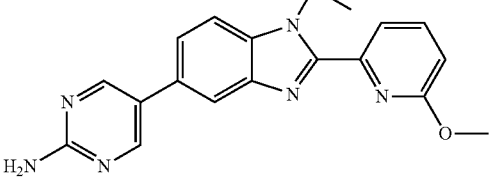
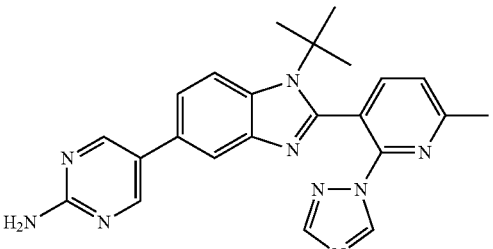
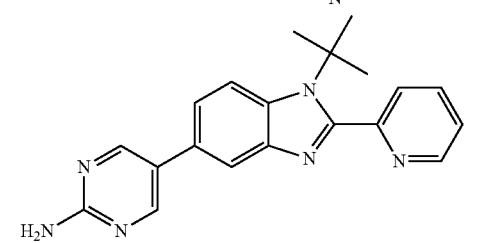
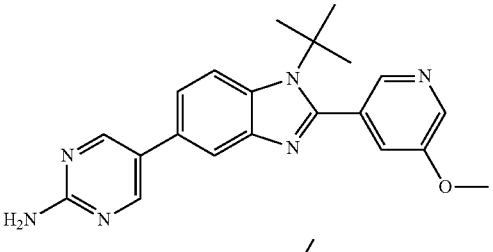
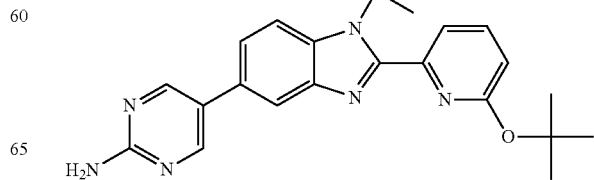

-continued
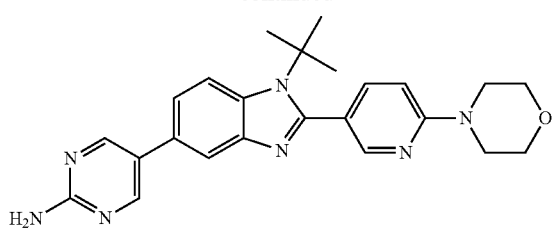
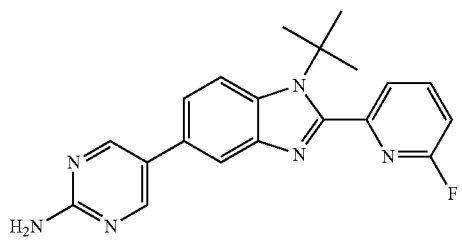
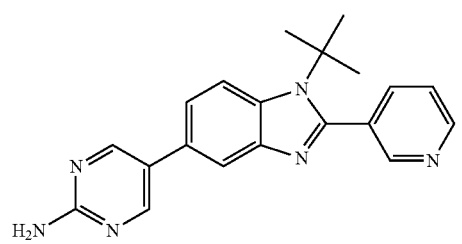
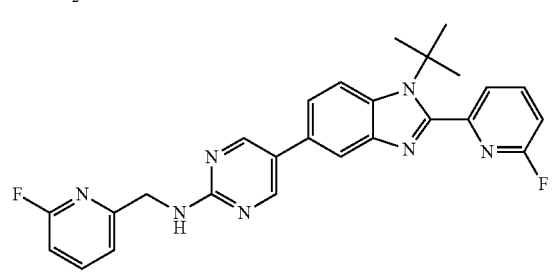
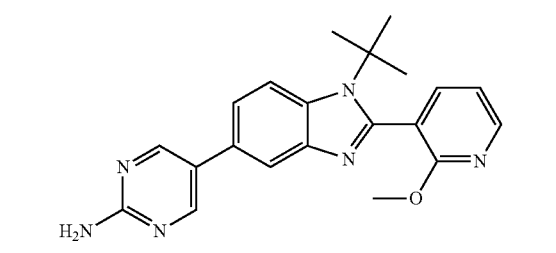
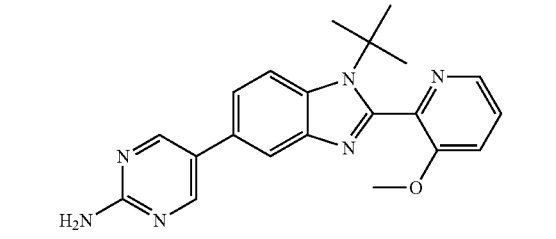
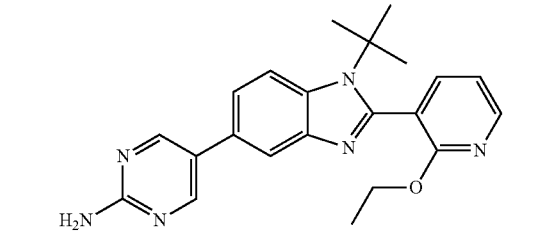
-continued
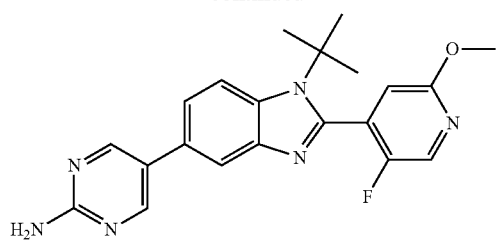
or pharmaceutically acceptable salts thereof.
31. A compound according to claim 30, selected from a group consisting of:
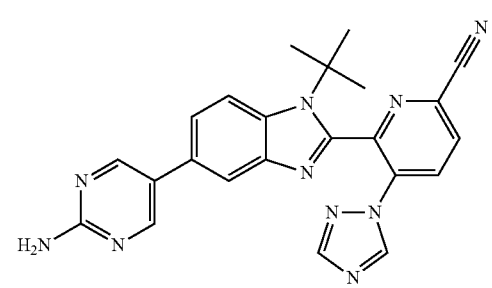
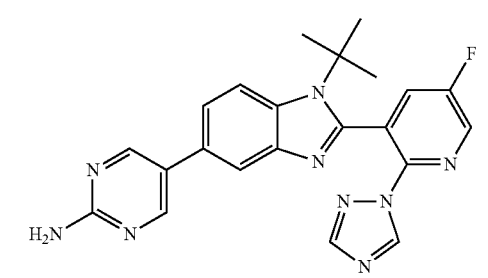
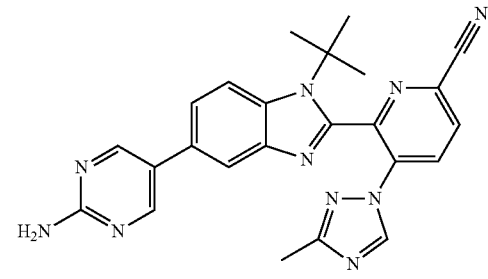
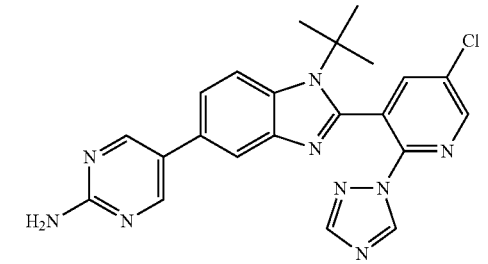

-continued
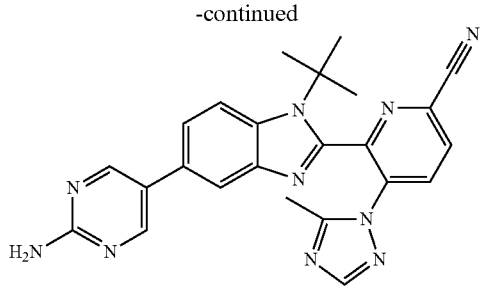
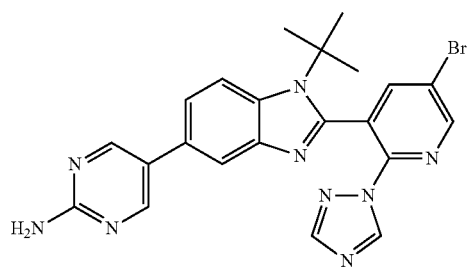
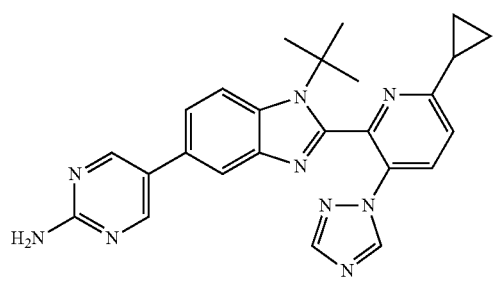
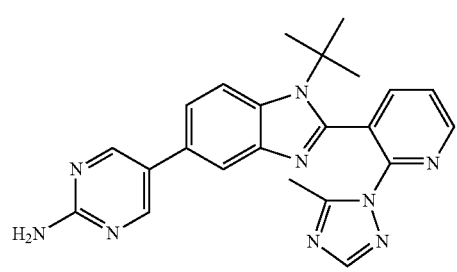
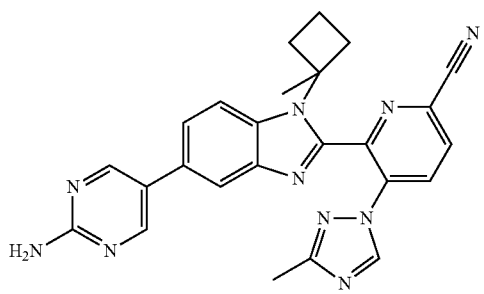
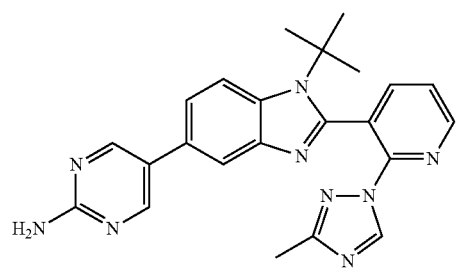
-continued
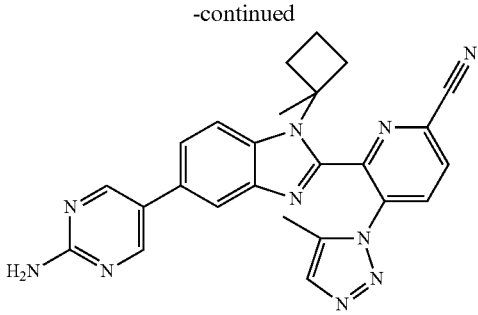
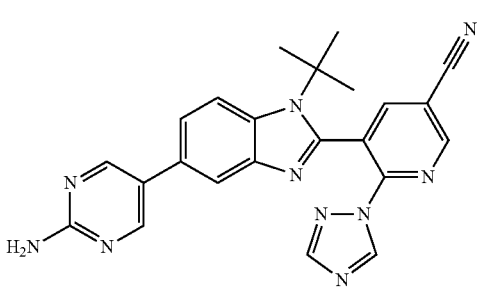
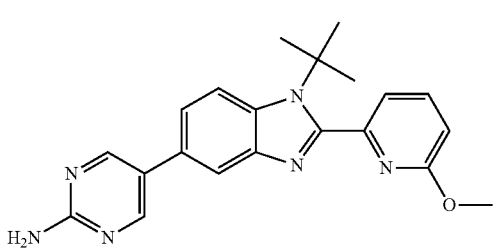
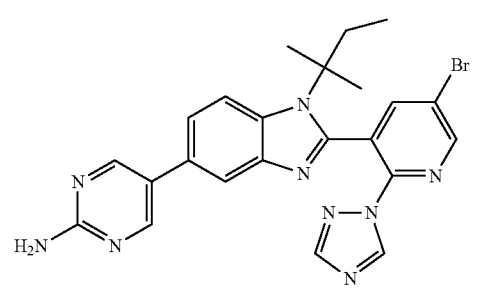
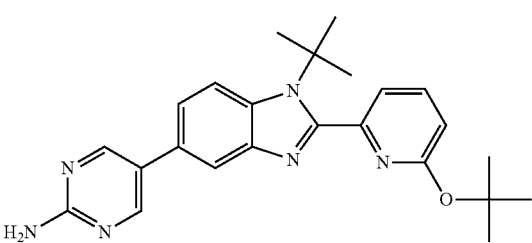
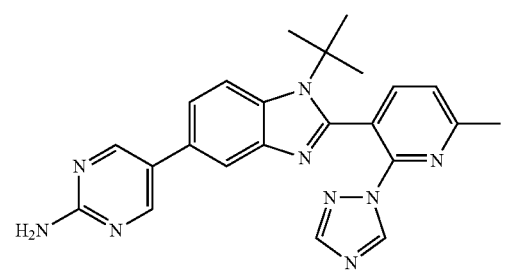

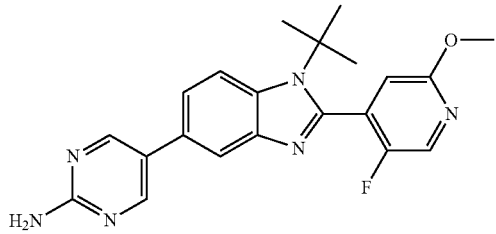
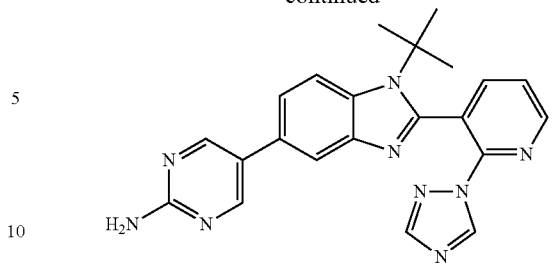

or pharmaceutically acceptable salts thereof.

32. A pharmaceutical composition comprising a compound according to claim 1, or a pharmaceutically acceptable salt thereof, and a pharmaceutically acceptable excipient and/or carrier.

33. A pharmaceutical composition comprising a compound according to claim 11, or a pharmaceutically acceptable salt thereof, and a pharmaceutically acceptable excipient and/or carrier.

34. A pharmaceutical composition comprising a compound according to claim 21, or a pharmaceutically acceptable salt thereof, and a pharmaceutically acceptable excipient and/or carrier.

* * * * *